(12) United States Patent
Takeda

(10) Patent No.: US 10,222,317 B2
(45) Date of Patent: Mar. 5, 2019

(54) METHOD FOR SORTING CELL PARTICLE IN SOLUTION

(71) Applicant: ON-CHIP BIOTECHNOLOGIES CO., LTD., Tokyo (JP)

(72) Inventor: Kazuo Takeda, Tokyo (JP)

(73) Assignee: On-Chip Biotechnologies Co., Ltd, Tokyo (JP)

( * ) Notice: Subject to any disclaimer, the term of this patent is extended or adjusted under 35 U.S.C. 154(b) by 0 days.

(21) Appl. No.: 14/923,747

(22) Filed: Oct. 27, 2015

(65) Prior Publication Data

US 2016/0139026 A1 May 19, 2016

Related U.S. Application Data

(63) Continuation of application No. 13/521,947, filed as application No. PCT/JP2011/050270 on Jan. 11, 2011, now Pat. No. 10,101,261.

(30) Foreign Application Priority Data

Jan. 15, 2010 (JP) ................................. 2010-007295

(51) Int. Cl.
*B01L 3/00* (2006.01)
*G01N 15/10* (2006.01)
*G01N 15/14* (2006.01)

(52) U.S. Cl.
CPC .... *G01N 15/1436* (2013.01); *B01L 3/502761* (2013.01); *G01N 15/1484* (2013.01); *B01L 3/502738* (2013.01); *B01L 3/502776* (2013.01); *B01L 2200/0652* (2013.01); *B01L 2300/0816* (2013.01); *B01L 2400/0487* (2013.01); *B01L 2400/0666* (2013.01); *B01L 2400/082* (2013.01); *G01N 2015/1006* (2013.01); *G01N 2015/149* (2013.01)

(58) Field of Classification Search
CPC ........... G01N 15/1436; G01N 15/1484; G01N 2015/1006; G01N 2015/149; B01L 3/502761; B01L 3/502738; B01L 3/502776; B01L 2200/0652; B01L 2300/0816; B01L 2400/0487; B01L 2400/0666; B01L 2400/082
See application file for complete search history.

(56) References Cited

PUBLICATIONS

Dittrich, Petra S., and Petra Schwille. "An integrated microfluidic system for reaction, high-sensitivity detection, and sorting of fluorescent cells and particles." Analytical chemistry 75.21 (2003): 5767-5774.*
Yang, Sung-Yi, et al. "A cell counting/sorting system incorporated with a microfabricated flow cytometer chip." Measurement Science and Technology17.7 (2006): 2001.*
Fu, Anne Y., et al. "A microfabricated fluorescence-activated cell sorter." Nature biotechnology 17.11 (1999): 1109.*

* cited by examiner

*Primary Examiner* — Robert J Eom
(74) *Attorney, Agent, or Firm* — Liang Legal Group, PLLC

(57) ABSTRACT

A method for sorting a cell particle in a solution includes steps of preparing an apparatus having a sample solution reservoir formed on a substrate, a main flow path formed in the substrate, a first branched flow path and a second branched flow path, and a downstream flow path; storing a sample solution; applying a constant gas pressure to the sample solution, illuminating the sample solution; determining calculating a delayed timing; and applying a pushing pressure.

6 Claims, 14 Drawing Sheets

Sorting flow path for "Pulling" or "Pushing": Sorting resolution >> Sorting flow path width Sorting flow paths for "Pulling" and "Pushing": Sorting resolution = Sorting flow path width Electromagnetic valve on Electromagnetic valve off

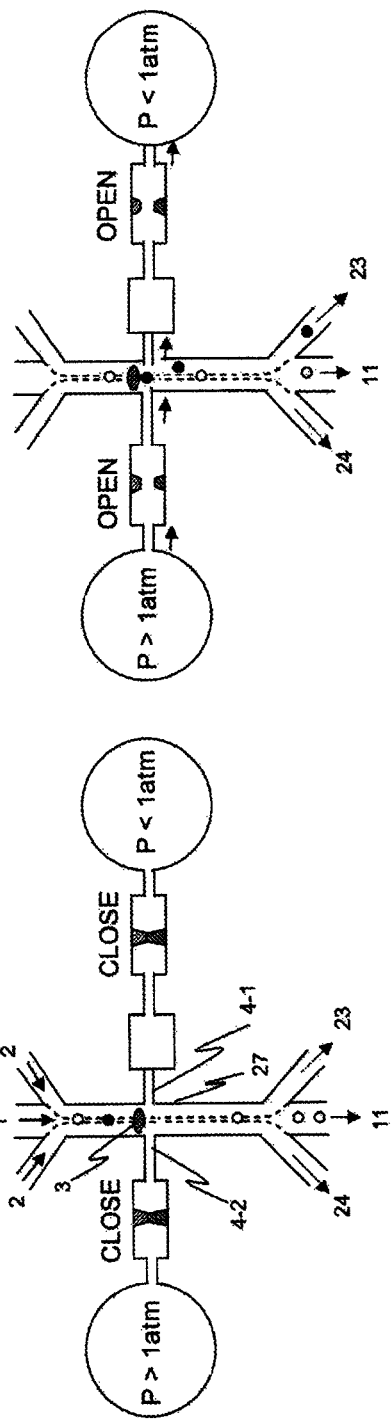

Measurement on flow path of left extremity

Measurement on flow path of right extremity

Data of sample containing air bubbles

Data of sample removing air bubbles

METHOD FOR SORTING CELL PARTICLE IN SOLUTION

CROSS-REFERENCE TO RELATED APPLICATIONS

The present application is a Continuation and claims benefit, pursuant to 35 U.S.C. § 120, of U.S. patent application Ser. No. 13/521,947 filed on Jul. 12, 2012, which is a national stage filing under 35 U.S.C. § 371 of International Application No. PCT/JP2011/050270 filed on Jan. 11, 2011, which claims priority of Japanese Patent Application No. 2010-007295 filed on Jan. 15, 2010, which are incorporated by reference in their entirety herein.

TECHNICAL FIELD

The present invention relates to an apparatus having a function to analyze biological particles typical of a flow cytometer or a function to separate biological particles typical of a cell sorter, a measurement method realizing a novel function using the same, and a disposable flow cell chip.

BACKGROUND ART

Flow cytometers are typically used to identify various types of cells and biological particles. Flow cytometers of the related art have an optically transparent flow cell made of quartz, formed with a flow path through which the cells to be individually identified flow. The flow of cells passing through the flow path is concentrated in the center portion of the flow path by a sheath liquid concentrically surrounding the flow of cells. The center portion of the flow path is illuminated with a laser beam. When a cell passes through an illumination region, light is scattered depending on the size, shape, and refractive index of the cell. To detect a cell specifically dyed with a fluorescent dye by fluorescence, the wavelength of the laser beam is determined in accordance with the type of the fluorescent dye. In this manner, the fluorescence as well as the scattered light for each of the cells is detected by multiple photodetectors based on the wavelength, enabling a diverse analysis of the cell. Technique of flow cytometry is described in Patent literature 1. A flat-plate flow cell is described in Japanese Patent Application Laid-Open (JP-A) No. 2003-302330 (Patent literature 10) and U.S. Pat. No. 7,105,355 (Patent literature 11). A flow cytometer using a disposable flow cell chip is described in U.S. Pat. No. 4,358,888 (Patent literature 14).

Existing cell sorting methods will now be described. The method described in U.S. Pat. No. 3,710,933 (Patent literature 1) or U.S. Pat. No. 3,826,364 (Patent literature 2) is a separation method currently adopted in common products. The method includes discharging droplets of a sample liquid from a nozzle for droplet formation into air, and separating the droplets which include the cells to be separated using an electric field. Japanese Patent Application Laid-Open (JP-A) No. 64-3541 (Patent literature 3) discloses a method that includes the steps of flowing a sheath flow at the periphery of a sample liquid flowing through a flow cell, and shifting charged particles from the sample flow to the sheath flow by applying an electric field to the sample liquid for separation and measurement. Japanese Patent Application Laid-Open (JP-A) No. 1-170853 (Patent literature 4) describes a method that includes a step of applying a pressure pulse to a particle flowing through a flow cell, and thus separating the particles into a flow path which is different from a flow path for steady flow in the flow cell. International Publication No. WO98/1026 (Patent literature 5) discloses a technique that includes applying a field to a flow of microparticles, the flow of which had been narrowed by a sheath flow in the flow cell, and shifting the flow of the microparticles for separation. International Publication No. WO2004/101731 (Patent literature 6) discloses a method of using gel electrodes disposed on both sides of a liquid flow path in a flow cell to apply a charge to the cell and then using an electric field to separate the cell. U.S. Pat. No. 6,808,075 (Patent literature 7) discloses a method that includes the steps of applying a pressure pulse by using a bubble valve forming a meniscus perpendicularly with respect to the flow of particles, and shifting the flow for separation. WO2006/076195 (Patent literature 8) discloses a method that includes a step of applying a pressure pulse as in Patent literature 5, but also includes steps of ejecting each droplet including target particle, and collecting them in a container. U.S. Pat. No. 4,756,427 (Patent literature 9) describes a method that includes steps of measuring each particle in a flow of sample liquid narrowed by a sheath flow, and if it is judged that the particle is a target particle, separating the particles using a piezoelectric element to generate a pulse flow to shift them into a different flow path.

The method for separating cells disclosed in Patent literature 12 is a method in which droplets containing cell flow in oil, and a static electric filed is used to apply a force to the droplet containing the target cell. Patent literature 13 discloses a method wherein a flow cell with branched-flow paths for cell sorting is used, and the target cells are introduced into a flow path for cell sorting by an intermittent flow produced using a piezoelectric element.

CITATION LIST

Patent Literature

[Patent literature 1] U.S. Pat. No. 3,710,933
[Patent literature 2] U.S. Pat. No. 3,826,364
[Patent literature 3] Japanese Unexamined Patent Publication (Kokai) No. 64-3541
[Patent literature 4] Japanese Unexamined Patent Publication (Kokai) No. 1-170853
[Patent literature 5] WO98/10267
[Patent literature 6] WO2004/101731
[Patent literature 7] U.S. Pat. No. 6,808,075
[Patent literature 8] WO2006/076195
[Patent literature 9] U.S. Pat. No. 4,756,427
[Patent literature 10] Japanese Unexamined Patent Publication (Kokai) No. 2003-302330
[Patent literature 11] U.S. Pat. No. 7,105,355
[Patent literature 12] WO2009/021215
[Patent literature 13] Japanese Unexamined Patent Publication (Kokai) No. 61-137062
[Patent literature 14] Japanese Patent No. 4358888

SUMMARY OF INVENTION

Technical Problem (1. Problems of the Liquid Flow System)

There is a biohazard problem in relation to conventional cell sorters. This is due to the possibility of foreign substances contaminating the measurement sample and the measurement sample being spread to outside. In other words, it is impossible for a conventional flow cytometer to readily change the solution flow system including the sample liquid reservoir, the liquid sending pipe, and the flow cell. Therefore, to prevent carry-over, the flow cytometer must be cleaned for each sample to be tested. This is also the case for a cell sorter which is a flow cytometer with an additional function of separation of microparticles. A solution to this is to make the flow cell disposable. When making the flow cell disposable, it is preferable that the flow cell has a flat-plate configuration like a glass slide. This is because a flat-plate flow cell enables mass production of flow path patterns easily and inexpensively by injection molding. When a flat-plate flow cell is used, it is preferable to apply an illumination laser perpendicular to the surface of the flow cell. However, there is a problem in detection of light scattered in to the plane of the substrate; that is, sideward scattered light. The detection of the scattered light, which gives information about the inner structure of cells, is an essential function in the general flow cytometer. The flow cell of the general flow cytometer typically has a square cross section, whereby a scattered light, perpendicular to the laser illumination direction is measured without any problems at the same time as the forward scattered light. However, when a flat-plate flow cell is used, the substrate of the flow cell is positioned in the direction of a sideward scattered light. Consequently, the flat-plate configuration of a flow cell results in an obstacle to measurement. As a method of solving this problem, Patent literature 11 describes a method that includes positioning an optical fiber on the side surface of a the flow path of a flow cell, and directing a light generated in the flow path to a photodetector. However, in this case, the optical fiber is connected to the flow cell, making the flow cell unsuitable for replacement after each measurement. Thus, this method is not applicable to a disposable flow cell. The flow cytometer using a disposable flow cell disclosed in Patent literature 14, which is a previous invention of the present inventors, does not have a function for detecting the sideward scattered light.

(2. Problems of the Flow Cell)

In addition, it is difficult to make the flow cell disposable unless it is manufactured at low cost. The flow cell is preferably made of a transparent resin in order to manufacture it inexpensively. However, the resin has a weak light absorption band in the region of a wavelength below 500 nm and generates fluorescence, resulting in background noise in measurements. In other words, in the case of a flow cell made of a transparent resin which is suitable for making it disposable, the self-fluorescence is an obstacle to measurement.

(3. Problem of a Method for Separating Cells)

A problem in relation to a microparticle separation method will now be discussed. This problem is a biohazard problem.

The method wherein droplets are discharged by a jet nozzle, and each of the droplet containing a target, cell is separated by an electric field (i.e. jet in air method), described in Patent literature 1 or Patent literature 2 has a biohazard problem: when the sample is a cell contaminated with pathogenic virus or bacteria, the method risks spreading a very dangerous substance as an aerosol into the atmosphere. In order to solve this problem, methods of separating the cell by confining the aerosol in the flow cell without spreading into the atmosphere have been considered. Some of these techniques have been published. Patent literature 3 discloses a method that includes steps of flowing a sheath flow around a sample solution flowing in a flow cell, and shifting charged particles from the sample flow to the sheath flow by applying an electric field to the sample solution, for separation and measurement. Patent literature 4 discloses a method that includes using a piezoelectric element to apply a pressure pulse to a particle flowing through a flow cell, and thus separating the particle into a flow path which is different from the flow path for steady flow in the flow cell. In this method, the separated particle does not return to the original flow path. A problem for this method in that forming a steady flow of air requires complex control. Patent literature 5 discloses a technique that includes applying an electric field or a magnetic field to particles flowing in a narrow flow surrounded by a sheath flow in a flow cell, and shifting the flow of the particles for separation. If an electric field is used as the field in this method, it corresponds to the method of Patent literature 3. A method that utilizes an electric field in the same way as that disclosed in Patent literature 6 is not suitable for practical use in sorting in electrolytes, even if the formation of bubbles by electrolysis is prevented by some means. This is because the electric charge on a cell is shielded by ions, contained in the electrolyte, surrounding the cell, resulting in the lowering of the force acting on the particles. Patent literature 7 discloses a technique for sorting of cells in a chip. In this method, a flow of a particle is shifted by means of a pressure from the lateral side so as to separate the particles in downstream. However, a reciprocating motion of a meniscus is required to apply the pressure, and flows in the forward and return directions are opposite. Consequently, the meniscus is required to return to the original position after the particle is moved away sufficiently. Patent literature 8 discloses a method that includes applying a physical impact pulse as in Patent literature 4, ejecting each droplet in a region including a target cell, and collecting it in a container. This cannot be realized in a disposable flow cell chip and has a problem of contamination with other samples. The technique disclosed in Patent literature 9 is not directly applicable to the disposable chip. Patent literature 12 discloses a method for separating cells wherein droplets containing a cell are flowed in oil, and target cells are separated by an electrostatic force acting on a charged droplet containing the target cell. This method has the advantage that, in oil, there are no ions which shield the electrostatic force, but has the disadvantage that the sorting speed of droplets bigger than cells is slow in oil with high viscosity. In the method for separating cells wherein the cells are introduced into a flow path by producing the intermittent flow using a piezoelectric element, disclosed in Patent literature 13, it is necessary to connect the piezoelectric element to the flow cell, which is not appropriate for the disposable chip. That is, a flow cell containing a piezoelectric element is expensive, and therefore the method is not applicable to the disposable chip.

(4. Problem of a Flow Cytometer for Multiple Samples)

A problem in relation to a flow cytometer for multiple samples will now be discussed. In general, when a number of samples are assayed using a conventional flow cytometer, a 96 well plate containing each sample in a separate well is placed on a stage capable of moving in the x, y, and z axes, and then the samples are assayed in order using a conventional flow cytometer. In this method, carry-over of samples and cross contamination of samples occur, because the system for supplying liquids is used repeatedly. To solve this problem, the present inventors think that a flow cell chip with multiple flow paths can be used, so as to assay a number of samples at a lower cost in less time. In this method, however, it is difficult to detect a sideward scattered light, as mentioned above. When a flow cell chip with multiple flow paths is used, as mentioned in Patent literature 11, it is proposed that an optical fiber is put on the side surface of each flow path of the flow cell, and the sideward scattered light is detected by directing the light through the optical fiber to a photodetector. However, a disposable flow cell chip containing an optical fiber is not suitable for practical use.

(5. Problems of Accurate Measurement of Cell Concentration Using A Disposable Flow Cell Chip)

A problem in relation to the measurement of cell concentration in a sample using a disposable flow cell chip will now be discussed. Cells are settled out by gravity. Therefore, the concentration of cells in the region close to the bottom of a sample tube rises with time. In order to avoid this phenomenon and obtain an accurate cell concentration, a measurement of the entire sample liquid is required. In the measurement of the entire sample liquid, the following problem occurs. For example, when the sample liquid is assayed using the flow cell chip disclosed in Patent literature 14, air bubbles are generated immediately after the completion of the passage of the sample liquid so that the data of the air bubbles is mixed with the measured data of the cells. The generation of the air bubbles disturbs the accurate measurement of number of cells in the sample liquid.

(6. Problems on Data Analysis)

A problem in relation to data analysis will now be discussed. Generally, in a flow cytometry analysis using multicolor staining, obtained values of fluorescences should be corrected. However, in the correction of the fluorescences, each value of the multiple fluorescences is corrected to each signal intensity because multiple signal intensities detected by multiple photodetectors have different wavelengths. Thus, an adjustment of the photodetector using a sample to be tested is required before measurement. Therefore, a sample labeled by multiple fluorescences for obtaining data, and samples each labeled by a single fluorescence are required. Further, the flow cytometer generally has three or more fluorescence detectors. That is, three or more sets of fluorescence data are obtained. In these circumstances, it is possible that the two dimensional data is presented in two dimensional graph. However, it is difficult for the conventional flow cytometer to analyse and present three dimensional data. In other words, in the conventional flow cytometer, the analysis and presentation of three dimensional data are carried out using multiple two dimensional representations or a three dimensional representation which can be rotated. Therefore, it is difficult to easily understand these three dimensional representations.

Under such circumstances, the object of the present invention is to provide an apparatus for analyzing, identifying and separating biological particles using the disposable chip-type flow cell mentioned below, and a disposable flow cell.

Namely, the present invention relates to:

[1] an apparatus for separating particles comprising:
  a flow cell wherein a flow path is formed in a flat substrate,
  a illumination unit configured to illuminate particles in a sample liquid flowing through the flow path,
  a detection unit configured to detect particles of interest by detecting a scattered light or fluorescence generated from the particle when the particle is illuminated, and identifying the particle based on its signal intensity,
  a constant-pressure pump which applies a pressure pulse to the particles in the sample liquid flowing through the flow path in the flow cell, and an electromagnetic valve connected thereto, and
  a control unit configured to control a movement of the electromagnetic valve based on the signal from the detection unit;

wherein the flow cell comprises:
  a flow path for introducing the sample liquid, and a pair of flow paths for introducing a sheath solution arranged on both sides of the flow path to introduce the sample liquid,
  a joining flow path for joining the flow path to introduce the sample liquid and the pair of flow paths to introduce the sheath liquid and flowing the sheath liquids on either side of the sample liquid,
  an illumination region on the joining flow path, and
  a pair of oppositely-branched flow paths connected to the joining flow path, downstream of the illumination region, wherein a first electromagnetic valve, which is normally closed, and a constant-pressure pump with a negative pressure are connected to one of the pair of oppositely-branched flow paths and a second electromagnetic valve, which is normally closed, and a constant-pressure pump with a positive pressure are connected to the other of the pair of oppositely-branched flow paths;
  and wherein the detection unit detects a light signal generated when the particles pass through the illumination region;

the control unit judges whether or not the particle is to be separated based on the light signal from the detection unit, and if it is judged that the particle is to be separated, a signal opening the electromagnetic valve for a short time is applied to both the first electromagnetic valve and the second electromagnetic valve, while the particle pass through the region of the joining flow path connected to the pair of oppositely-branched flow paths, so that push and pull pressures are respectively applied from the pair of oppositely-branched flow paths to the particle of interest flowing through the region, and the particle of interest is separated by altering the flow route of the particle;

[2] the apparatus for separating particles of the item [1], wherein if it is judged that the particle is to be separated, the control unit applies a signal opening the electromagnetic valve for a short time to the electromagnetic valves while the particles pass through the region of the joining flow path connected to the pair of oppositely-branched flow paths, so that push and pull pressures are applied to the particle of interest in the region, and the particle of interest is separated to the branched flow path of the pull pressure side by altering the flowing route of the particle;

[3] the apparatus for separating particles of the item [1], wherein the flow cell further comprises a pair of additional branched flow paths branching from the joining flow path downstream of the region connected to the pair of oppositely-branched flow paths,
  if it is judged that the particle is to be separated, the control unit applies a signal opening the electromagnetic valve for a short time to the electromagnetic valves while the particles pass through the region of the joining flow path connected to the first pair of oppositely-branched flow paths, so that push and pull pressures are applied to the particle of interest in the region of the joining flow path between the first branched flow paths, and the particle of interest is separated into the additional branched flow path by altering the flow route of the particle:

[4] a flat-plate flow cell for separating particles contained in a sample liquid while the sample liquid flows through a flow path, wherein the flow path is formed in a transparent substrate, and reservoirs fluidly connected to the flow path are formed at the upstream and downstream ends of the flow path; and wherein the transparent substrate comprises:
a flow path for introduction of a sample liquid;
a pair of flow paths for introduction of a sheath liquid, arranged on both alongside of the flow path for introduction of the sample liquid;
a joining flow path for joining the flow path for introduction of a sample liquid and the pair of flow paths for introduction of a sheath liquid, in which the sheath liquid flows both alongside of the sample liquid; and a pair of oppositely-branched flow paths connected to a side surface of the joining flow path, equipping ports capable of air tight connection to external pumps;

[5] a flow cytometer for multiple samples, wherein a sample liquid is illuminated with light while the sample liquid containing biological particles flows through a flow path in the flow cell, and light generated from particles contained in the sample liquid is detected:
characterized in that:
the flow cytometer comprises:
a stage for placing the flow cell,
an illumination unit,
a detection unit for detecting the biological particles, and
a control unit configured to control movements of the above parts:
the flow cell is flat-plate, wherein multiple sample liquid reservoirs, multiple sheath liquid reservoirs, multiple discharged liquid reservoirs, multiple collected sample liquid reservoirs, and multiple flow paths fluidly connected thereto, are formed on a flat-plate substrate;
each of the sample liquid reservoirs is separately formed in each of sheath liquid reservoirs so as not to mix the liquids,
each of flow paths for sample liquid is connected to each of the sample liquid reservoirs,
a pair of flow paths for sheath liquid are connected to each of the sheath liquid reservoirs,
the pair of flow paths for sheath liquid are connected to a side surface of each of flow paths for sample liquid,
a joining flow path in which sheath flows are joined to a sample flow from the left and right sides of the sample liquid flows is formed, by connecting the pair of flow paths for sheath liquid to the flow path for sample liquid, the joining flow paths are formed so as to be parallel at equally spaced intervals, and the downstream end of the joining flow path is connected to the discharged liquid reservoir and the collected sample liquid reservoir formed on the flow cells; and
each of the flow paths is illuminated in sequence by moving an illumination light relative to the flow cell, or the flow cell relative to the light (by step and repeat) using a light beam that illuminates only one flow path at a time, so that multiple samples are analyzed;

[6] the flow cytometer for multiple samples of the item [5], wherein the flow cell has inclined surfaces at both ends of the lateral side of the transparent substrate, whereby a sideward scattered light generated in each of the flow paths is detected by total reflection at both ends;

[7] a flow cytometer comprising an illumination light source, and a fluorescence measuring device configured to measure multiple fluorescences at different, wavelengths;
wherein the flow cytometer comprises:
a unit for analyzing and showing a distribution cells, based on the intensity ratio of fluorescence at two different wavelengths generated by illumination with a light, in the analysis of cells having more than one fluorescence, and
a unit for estimating a quantitative ratio of multiple fluorescences in each of the cells based on the intensity ratio;

[8] an apparatus for measuring a particle in a liquid, characterized in that the apparatus comprises:
a flow cell wherein a flow path is formed in a flat substrate,
a illumination light source which illuminates particles contained in sample liquid, while the particles and a sheath liquid flow through a flow path in the flow cell,
a detection unit configured to detect particles of interest by detecting scattered light or fluorescence generated from a particle when the particle is illuminated, and identifying the particle based on its signal intensity,
a control and analysis unit configured to control the above parts and analyze the particles based on information from the detection unit,
wherein the end point of the sample liquid is detected by a signal from air bubbles generated when the sample liquid is finished, so that the total number of particles contained in sample liquid are measured;

[9] an apparatus for measuring a biological particle.
characterized in that the apparatus comprises: an illumination light, source,
a light measuring device configured to measure intensities of light generated from each particle by illumination with light in multiple wavelength ranges, and an unit for analyzing a property of the particle wherein the property of the particle is analyzed by an index obtained by calculating multiple signal intensities corresponding to multiple measurement aspects of the particle;

[10] the apparatus for measuring a biological particle of the item [9],
wherein the apparatus further comprises
a calculation unit for judging whether the biological particle is a dead cell or live cell, based on the value of an index obtained for each particle by calculating an intensity ratio of fluorescence signals at two different wavelengths generated by illumination with a light, when cells or bacteria which are stained simultaneously by a dye capable of penetrating cell membrane and a dye not capable of penetrating cell membrane are judged whether the cells or bacteria are dead or alive;

[11] an apparatus for measuring a biological particle,
characterized in that the apparatus comprises:
an illumination light source, and
a light measuring device configured to measure intensities of light generated from each cells by illumination with light in multiple wavelength ranges, wherein an index of each particle identified by a mathematical formula using multiple signal intensities is calculated, and the index can be displayed on a graph to illustrate data relating to the particles.

Advantageous Effects of Invention

According to the present invention,
(1) a cell sorter,
(2) a flow cytometer capable of detecting sideward scattered light,
(3) a method for accurately measuring cell concentration,
(4) a method for multicolor staining analysis without a fluorescence correction, and the like which satisfy requirements that a carry-over and a cross contamination of samples do not occur,
are provided.

BRIEF DESCRIPTION OF THE DRAWINGS

FIG. 3A shows a second embodiment of the cell sorter according to the present invention with the electromagnetic valve in the off state (Close). FIG. 3B shows a second embodiment of the cell sorter according to the present invention with the electromagnetic valve in the on state (Open).

DESCRIPTION OF EMBODIMENTS

1. Apparatus for Separating Particles

Figure 1A:
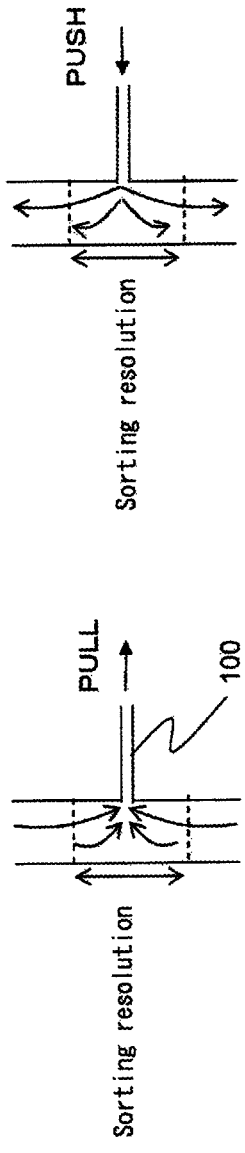
FIG. 1A is a view showing a problem as to the cell sorting in a flow path using a pulse flow.

An apparatus for separating particles is provided, as an embodiment of the present invention. The apparatus for separating particles typically comprises:
(i) a flow cell wherein a flow path is formed in a flat substrate,
(ii) a illumination unit configured to illuminate particles in a sample liquid flowing through the flow path,
(iii) a detection unit configured to detect particles of interest by detecting scattered light or fluorescence generated from the particle when the particle is illuminated, and identifying the particle based on its signal intensity,
(iv) a constant-pressure pump which applies a pressure pulse to the particles in the sample liquid flowing through the flow path in the flow cell, and an electromagnetic valve connected thereto, and
(v) a control unit configured to control movement of the electromagnetic valve based on the signal from the detection unit.

The flow cell typically comprises:
(a) a flow path for introducing the sample liquid, and a pair of flow paths for introducing a sheath solution arranged on both sides of the flow path to introduce the sample liquid,
(b) a joining flow path for joining the flow path to introduce the sample liquid and the pair of flow paths to introduce the sheath liquid and flowing the sheath liquids on either side of the sample liquid in the joining flow path,
(c) an illumination region on the joining flow path, and
(d) a pair of oppositely-branched flow paths connected to the joining flow path at an angle of about 90 degrees, downstream of the illumination region.

Typically, a first electromagnetic valve, which is normally closed, and a constant-pressure pump with a negative pressure are connected to one of the pair of oppositely-branched flow paths and a second electromagnetic valve, which is normally closed, and a constant-pressure pump with a positive pressure are connected to the other of the pair of oppositely-branched flow paths.

Typically, the detection unit detects a light signal generated when the particles pass through the illumination region.

Typically, the control unit judges whether or not the particle is to be separated based on the light signal from the detection unit, and if it is judged that the particle is to be separated, a signal opening the electromagnetic valve for a short time is applied to both the first electromagnetic valve and the second electromagnetic valve, while the particle pass through the region of the joining flow path connected to the pair of oppositely-branched flow paths, so that push and pull pressures are respectively applied from the pair of oppositely-branched flow paths to the particle of interest flowing through the region, and the particle of interest is separated by altering the flow route of the particle.

Alternatively, in the apparatus for separating particles of the present invention, when it is judged that the particle is to be separated, the control unit applies a signal opening the electromagnetic valve for a short time to the electromagnetic valves while the particles pass through the region of the joining flow path connected to the pair of oppositely-branched flow paths, so that push and pull pressures are applied to the particle of interest in the region, and the particle of interest may be separated to the branched flow path of the pull pressure side by altering the state of flowing of the particle.

In the apparatus for separating particles of the present invention, the flow cell further may comprise a pair of additional branched flow paths branching from the joining flow path downstream of the region connected to the pair of oppositely-branched flow paths. Further, if it is judged that the particle is to be separated, the control unit applies a signal opening the electromagnetic valve for a short time to the electromagnetic valves while the particles pass through the region of the joining flow path connected to the first pair of oppositely-branched flow paths, so that push and pull pressures are applied to the particle of interest in the region of the joining flow path between the first branched flow paths, and the particle of interest is separated into the additional branched flow path by altering the flow route of the particle.

2. A Flat-plate Flow Cell

As another embodiment of the present, invention, a flat-plate flow cell for separating particles contained in a sample liquid while the sample liquid flows through a flow path, is provided. In the typical flat-plate flow cell, the flow path is formed in a transparent substrate, and reservoirs fluidly connected to the flow path are formed at the upstream and downstream ends of the flow path.

More specifically, the flow cell comprises:
(i) a flow path for introduction of a sample liquid; and a pair of flow paths for introduction of a sheath liquid, arranged on both sides of the flow path for introduction of the sample liquid:
(ii) a joining flow path for joining the flow path for introduction of a sample liquid and the pair of flow paths for introduction of a sheath liquid, in which the sheath liquid flows along either side of the sample liquid; and
(iii) a pair of oppositely-branched flow paths connected to the sides surface of the joining flow path at an angle of about 90 degrees; which are formed on the transparent substrate.

Further, (iv) each of the oppositely-branched flow paths has a port capable of air tight connection to an external pump.

The flow cell may comprise a pair of additional branched flow paths branching from the joining flow path downstream of the region connected to the pair of oppositely-branched flow paths.

3. Flow Cytometer for Multiple Samples

Further, as another embodiment of the present invention, a flow cytometer for multiple samples, wherein a sample liquid is illuminated with light while the sample liquid containing biological particles flows through the flow path in the flow cell, and light generated from particles contained in the sample liquid is detected, is provided. The flow cytometer typically comprises:
(i) a stage to hold the flow cell,
(ii) an illumination unit,
(iii) a detection unit for detecting the biological particles, and
(iv) a control unit configured to control movements of the above parts.

The flow cell may be flat-plate. Further, in the flow cell, multiple sample liquid reservoirs, multiple sheath liquid reservoirs, multiple discharged liquid reservoirs, multiple collected sample liquid reservoirs, and multiple flow paths fluidly connected thereto, may be formed on a flat-plate substrate. In addition, each of the sample liquid reservoirs may be separately formed in each of sheath liquid reservoirs so as not to mix the liquids. Furthermore, each of flow paths for sample liquid may be connected to each of the sample liquid reservoirs. Further, a pair of flow paths for sheath liquid may be connected to each of the sheath liquid reservoirs. Furthermore, the pair of flow paths for sheath liquid may be connected to the sides surface of each of flow paths for sample liquid.

The joining flow path in which sheath flows are joined to a sample flow from the left and right sides of the sample liquid flows may be formed, by connecting the pair of flow paths for sheath liquid to the flow path for sample liquid. The joining flow paths may be parallel at equally spaced intervals, and the downstream end of the joining flow path may be connected to the discharged liquid reservoir and the collected sample liquid reservoir formed on the flow cells.

According to the flow cytometer for multiple samples of the present invention, each of the flow paths is illuminated in sequence by moving an illumination light relative to the flow cell, or the flow cell relative to the illumination light (by step and repeat) using a light beam that illuminates only one flow path at a time, so that multiple samples can be analyzed.

In the flow cytometer for multiple samples of the present invention, the flow cell may have inclined surfaces at both ends of the lateral side of the transparent substrate, whereby a sideward scattered light generated in each of the flow paths may be detected by total reflection at both ends.

4. Other Flow Cytometers

Further, as another embodiment of the present invention, the flow cytometer comprising: a unit for analyzing and showing a distribution of cells, based on the intensity ratio of fluorescence at two different wavelengths generated by illumination with a light, in the analysis of cells having more than one fluorescence; and a unit for estimating a quantitative ratio of multiple fluorescences in each of the cells based on the intensity ratio, is provided. Furthermore, as another embodiment of the present invention, when cells or bacteria which are stained simultaneously by a dye capable of penetrating the cell membrane and a dye not capable of penetrating the cell membrane are analyzed, an apparatus for measuring a biological particle is provided, wherein the apparatus comprises a calculation unit for judging whether the cells or bacteria are dead or alive by determining whether an intensity ratio of fluorescence signals at two different wavelengths generated by illumination with a laser light is more or less than a predetermined reference ratio.

The flow cytometer or the apparatus for measuring biological particles typically comprises a laser illumination light source, and a fluorescence measuring device configured to measure multiple fluorescences at different, wavelengths.

The particular embodiments of the present invention will now be further illustrated by referring to the figures, but is by no means limited to the these embodiments.

1) Method for Separating Cells, and Apparatus for Separating Cells

The method for separating cells and the apparatus for separating cells, which can carry out a cell separation in the disposable chip, of the present invention will be explained in detail with reference to FIGS. 1A and 1B. FIG. 1A shows flows generated when a pressure is applied to the main flow path from a cell sorting flow path 100 connected to a side surface of the main flow path. When a negative pressure much lower than the pressure in the main flow path is applied to the main flow path, the flow is drawn into the cell sorting flow path (i.e. PULL state). When a positive pressure much higher than the pressure in the main flow path is applied to the main flow path, the flow is from the cell sorting flow path 100 to the main flow path (i.e. PUSH state). It is impossible to move only a cell of interest by applying the negative or positive pressure, when the cell, which flows in the main flow path, cuts across in front of the cell sorting flow path. In other words, when a particular cell only is separated to a separating flow path by the pressure, the pressure spreads to a broad range of the liquids. Therefore, a spatial resolution for separation is poor.

Figure 1B:
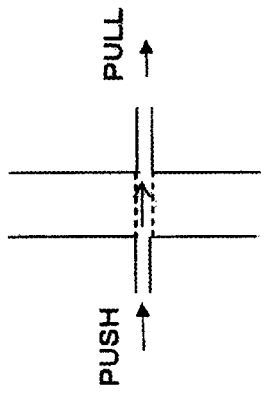
FIG. 1B is a view showing the principle for solving the above problem according to the present invention.

With the aim of solving the aforementioned problems, as shown in FIG. 1B. Under normal conditions, there is no flow between the main flow path and the sorting flow paths. Then, only when the cell of interest passes through the region where the sorting flow paths are located oppositely, a negative pressure and a positive pressure are generated from the sorting flow paths. In this case, a region wherein the pressures from the sorting flow paths act on liquids in the main flow path, may be limited to just the approximate width of the sorting flow paths by nearly matching the "pushed" flow volume to the "Pulled" flow volume. This method is shown in FIGS. 2A and 2B.

Figure 2B:
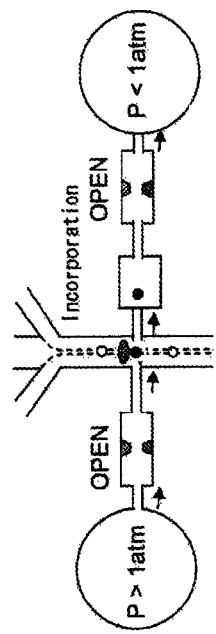
FIG. 2B shows an example of the cell sorter according to the present invention with the electromagnetic valve in the on state (Open).
Figure 2A:
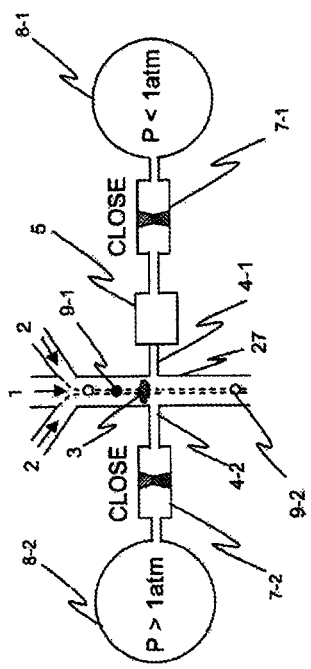
FIG. 2A shows an example of the cell sorter according to the present invention with the electromagnetic valve in the off state (Close).

As shown in FIGS. 2A and 2B, a sample liquid containing cells flows in the flow path 1 formed in the flow cell, and a sheath liquid not containing cells flows in the flow paths 2. Then, the sample liquid and the sheath liquid are joined so that a thin sample liquid flows in a joining flow path. Two branched flow paths 4-1 and 4-2 are connected to sides of the flow path in which the sample liquid flows. The flow path 4-1 is for "Pulling", and the flow path 4-2 is for "rushing". A reservoir 5 capable of reserving the cells of interest, an electromagnetic valve 7-1, and a cylinder pump 8-1 are connected to the flow path 4-1. The cylinder pump 8-1 maintains a constant pressure much lower than the pressure in the flow path 1. An electromagnetic valve 7-2, and a cylinder pump 8-2 are connected to the flow path 4-2 for "Pushing". The cylinder pump 8-2 maintains a constant pressure much higher than the pressure in the flow path 1. When the cells contained in the sample liquid pass through a laser illumination region 3, scattered light or fluorescence is generated from the cells. The scattered light or fluorescence is detected by the photodetector and the signal intensity thereof is quantified, and then the signal intensity is compared to a predetermined signal intensity for cells to be separated. Then, it is determined by a signal processing circuit whether or not the cell is one to be separated. If the cell is one to be separated, a trigger signal is generated when the cell passes through a front of the branched flow paths. The trigger signal maintains electromagnetic valves 7-1 and 7-2 in the open state for a short time. During the open state, a certain flow volume is passed to the separating flow path 4-1 from the main flow path, and the flow path 4-2 feeds to main flow path the same flow volume. As a consequence, the flow for sorting is limited to a region between the flow path 4-1 and flow path 4-2, broadening of the spatial resolution for the cell separation compared to the width of the flow path 4-1, can be prevented. In this operation, in order to generate a pressure pulse, the constant-pressure pump and the electromagnetic valve are connected, so that the pressure for sorting cells and the duration for sorting cells are independently controlled. The constant-pressure pump is an appropriate countermeasure against biohazard because aerosols are not generated from the constant-pressure pump.

When the flow rate generated by the sorting flow paths for "Pushing" and for "Pulling" is slower than the one of flow path 27, the cell of interest cannot be sorted into the sorting reservoir 5. In this case, the method for separating cells shown in FIGS. 3A and 3B is used. FIG. 3A shows the off state (Close) of the electromagnetic valve. Downstream of the flow path 27, flow paths 11, 23, and 24 are formed symmetrically to the flow paths 1, 2, and 2. Due to the hydrodynamic effect in laminar flow, the sheath liquids flow separately to the flow paths 23 and 24, and the sample liquid 1 is collected in the flow path 11. FIG. 3B shows the on state (Open) of the electromagnetic valve. In this instance, the position of the cell of interest is slightly shifted to the side of the flow path 4-1 by the flow generated by the pressures from the flow paths 4-1 and 4-2, and then the cell of interest flows in the flow path 27 while retaining its shifted route. Therefore, due to the shift of the position, the cell of interest is separated to the flow path 23 at the downstream end.

If necessary, a filter is equipped, in order to prevent an inflow of cells or bacteria to the electromagnetic valve. The filter is useful to prevent the cells or bacteria being mixed into flow path from outside of the flow cell, and prevent the spread of samples outside of the flow cell.

An embodiment for separating cells in the disposable chip will be explained using FIG. 4 and FIG. 5.

Figure 4:
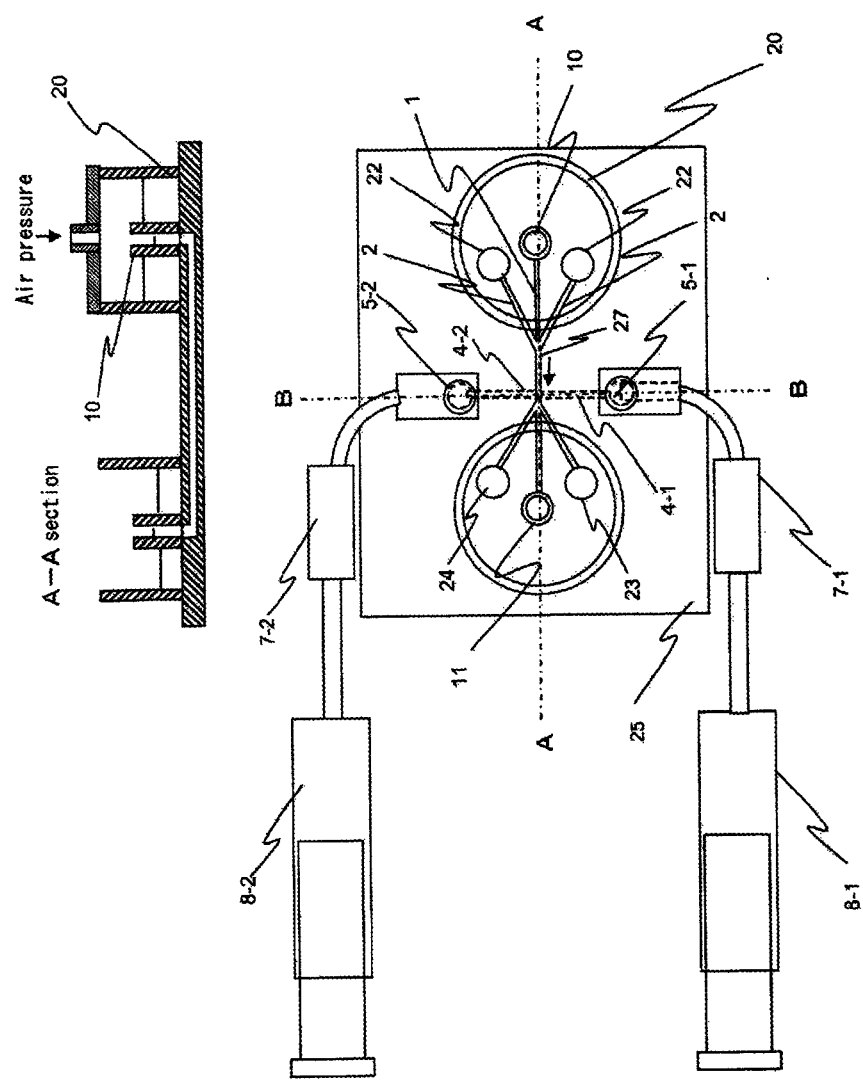
FIG. 4 is a view showing a configuration of the flow cell, the electromagnetic valve, and the constant-pressure pump, for cell separation using the disposable chip-type flow cell according to the present invention.

FIG. 4 shows the disposable chip-type flow cell to which the cylinder pump and the electromagnetic valve are connected. The disposable chip used in the present invention has a configuration wherein the flow paths 4-1 and 4-2 illustrated in FIGS. 2A and 2B are symmetrically connected to the disposable chip disclosed in Patent literature 14, and further the sorting reservoirs 5-1 and 5-2 are symmetrically connected thereto. The disposable chip-type flow cell is made of transparent resin. As the resin, poly methyl methacrylate (PMMA), cyclo olefin copolymer (COC), methylpentene polymer, or the like can be used. In particular, when a laser having a wavelength range in the UV region between about 350 nm to 410 nm is used as an illumination light source, methylpentene polymer is appropriate as a material of the flow cell. Symmetrically across the flow path 27, the sorting reservoir is connected to flow path 4-2, and electromagnetic valve and cylinder pump are connected to the sorting reservoir. Due to the symmetric structure, when the electromagnetic valves open, equivalent pressures are applied to the flow path 27 for an equivalent time.

Figure 5:
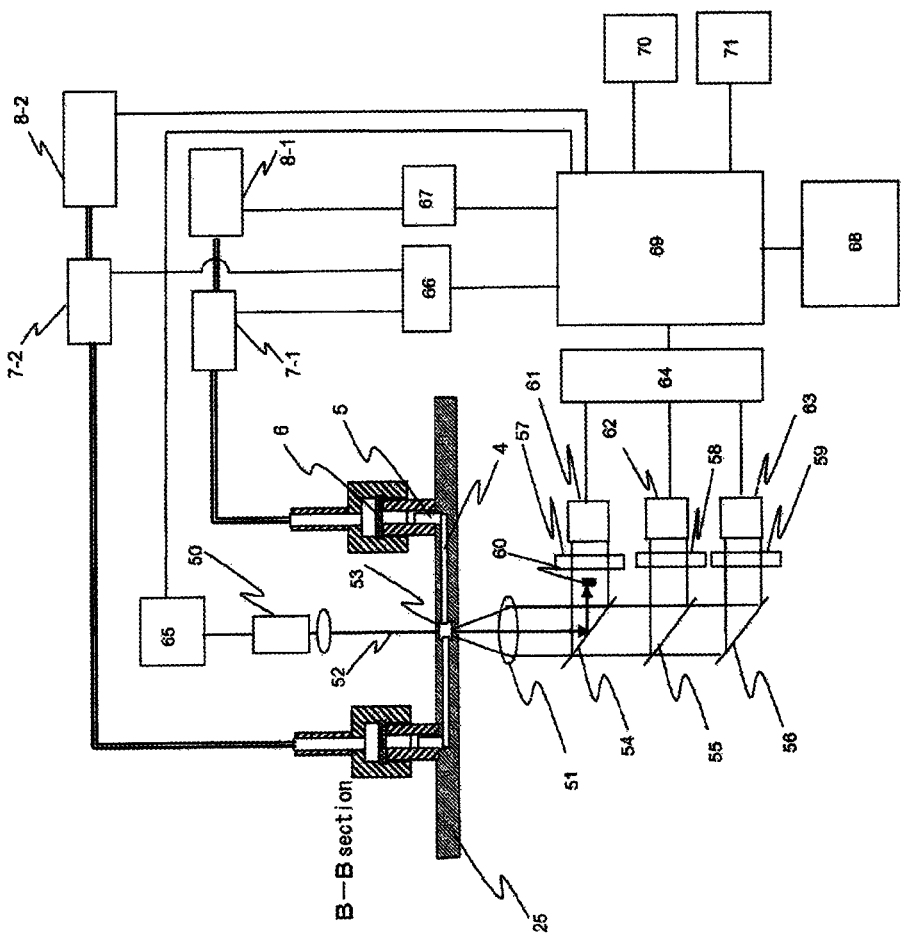
FIG. 5 is a view showing the flow cell, the optical system, and the control system, for cell separation using the disposable chip-type flow cell according to the present invention.

FIG. 5 shows the connection of the optical system and the control circuit. The cross-sectional view of the chip is taken along BB of FIG. 4. As shown in FIG. 4, an air pressure is applied at the upstream end of the flow path, so that the sample liquid together with the sheath liquid is flowed into the flow path 27. Then a laser light 52 illuminates the central part of the main flow path, which is at a position slight, upstream of the region of oppositely-branched flow paths 4-1 and 4-2. The instant that the cell passes through the illumination region, a pulse of scattered light or fluorescence is generated in pulses. In the detection of the scattered light, the same wavelength as the laser illumination light is selected by a dichroic mirror 54 and a band pass filter 57, and then the scattered light is detected by the detector 61. Transmitted laser light is removed by positioning the shielding plate 60 in front of the detector 61. In the detection of fluorescence, the fluorescences are divided into several wavelength regions by dichroic mirrors 55 and 56 and band pass filters 58 and 59 at wavelengths longer than the wavelength of the illumination laser light, and detected by detectors 62 and 63 respectively. The detected pulse signals are digitalized by a circuit 64 capable of amplification and analog-digital conversion, and microcomputer 69 determines whether the multiple detected signals meet predetermined parameters for separating cell. If the signals meet the parameters, the trigger signal is fed to an electromagnetic valve driver 66 after a fixed delay time from the signal detection. The delay time is the time taken for a cell to flow from the laser illumination region to the region between the sorting flow paths 4-1 and 4-2. The electromagnetic valve driver 66 which receives the trigger signal, feeds signals to the electromagnetic valves 7-1 and 7-2, opening them for a predetermined time. The predetermined time for opening the valves is preferably W/V (minutes) wherein W is an equivalent width of flow path 4-1 and flow path 4-2, and V is a flow rate of cell in the flow path 27. The cell of interest flows into the sorting reservoir 5, when the electromagnetic valves open. There is no flow from the main flow path to the sorting flow path when valves 7-1 and 7-2 are closed. Thus, once incorporated into the sorting reservoir the cells are stably preserved.

As shown in FIG. 4, a predetermined air pressure may apply to the inside of the reservoir 20 positioned at the upstream end of the chip by a constant-pressure pump which is not shown in FIG. 4. A sample reservoir 10 is formed in the reservoir 20, and the sample liquid is poured into the sample reservoir and the sheath liquid is poured into the outside of the sample reservoir. Phosphate buffer saline (PBS) is preferably used as the sheath liquid. The air pressure common to the sample reservoir and the reservoir 20, causes the sample liquid 1 and the sheath liquid 2 to the right and left of the sample liquid to flow downstream. The three flow paths are joined and the sample liquid flows thinly in the joining flow path 27 while surrounded by the sheath liquids. The width of the flow path 27 is 80 µm and a depth thereof is 50 µm. The width of the sample liquid after joining is about one-tenth of the width of the flow path. The flow path 27 has the oppositely-branched sorting flow paths 4-1 and 4-2 on sides thereof, and the oppositely-branched sorting flow paths connect with the reservoir 5. A laser light 52 having a wavelength of 488 nm is illuminated on a central region of the flow path 27 which is a few hundred micrometers upstream of the region of the oppositely-branched sorting flow paths. The size of the laser beam is oval having a length of 50 µm and a width of 20 µm.

The instant that the cell passes through the illumination region, a scattered light or fluorescence is generated in pulses. In the detection of the scattered light, the same wavelength as the laser illumination light is selected by a dichroic mirror 54 and a band pass filter 57, and then the scattered light is detected by the detector 61. The transmitted laser light is removed by positioning the shielding plate 60 in front of the detector 61. In the detection of fluorescence, the fluorescences are divided into multiple wavelength regions via dichroic mirrors 55 and 56 and band pass filters 58 and 59 at wavelengths longer than the wavelength of the illumination laser light, and detected by detectors 62 and 63 respectively. The detected pulse signals are digitalized by a circuit 64 capable of amplification and analog-digital conversion, and a microcomputer 69 determines whether the multiple detected signals meet predetermined parameters for separating cells. If the signals meet the parameters, the trigger signal is fed to an electromagnetic valve driver 66 after a fixed delay time from the signal detection. The delay time is the time taken for a cell to flow from the laser illumination region to the region between the sorting flow paths 4-1 and 4-2. The electromagnetic valve driver 66 which receives the trigger signal, feeds signals to the electromagnetic valves 7-1 and 7-2, opening them for a predetermined time. The predetermined time for opening the valves is preferably W/V (minutes) wherein W is an equivalent width of flow path 4-1 and flow path 4-2, and V is a flow rate of cell in the flow path 27. The cell of interest flows into the sorting reservoir 5-1, when the electromagnetic valves open. There is no flow from the main flow path to the sorting flow path when valves 7-1 and 7-2, are closed. Thus, once incorporated into the sorting reservoir the cells are stably preserved. In the flow cell showed in FIG. 4, the separating flow paths 11, 23, and 24 are formed at the downstream end. When the cell of interest does not move into the sorting reservoir 5-1 by the pressure which is generated by the flow paths 4-1 and 4-2, the cell of interest is separated to the flow path 23 at the downstream end. Therefore, in the flow cell shown in FIG. 4, when the flow rate in the flow path 27 is fast, the cell is separated to the flow path 23. When the flow rate in the flow path 27 is slow, the cell is separated to the sorting reservoir 5-1. That is, the flow cell of the present invention has a flexible configuration wherein the above two separation methods can be carried out in response to the flow rates of the flow path 27.

Figure 6:
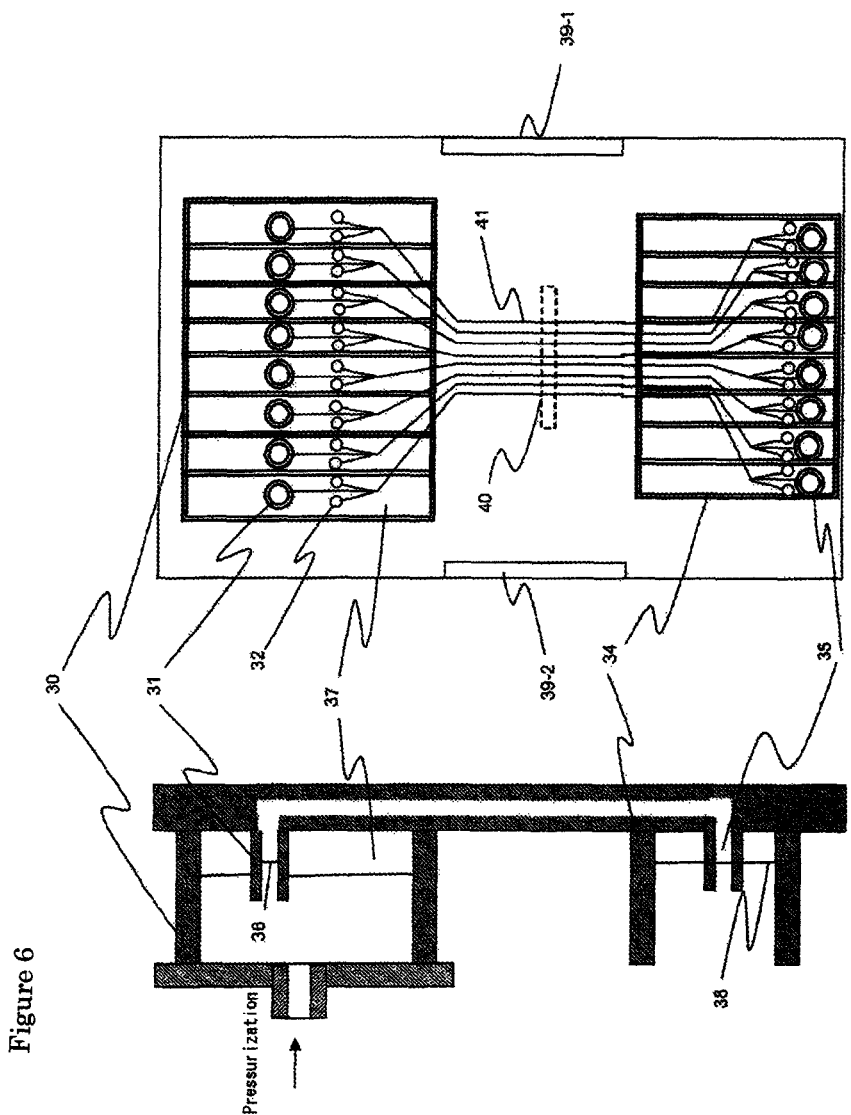
FIG. 6 is a view showing a configuration of the disposable chip-type flow cell for multiple samples according to the present invention.
Figure 7:
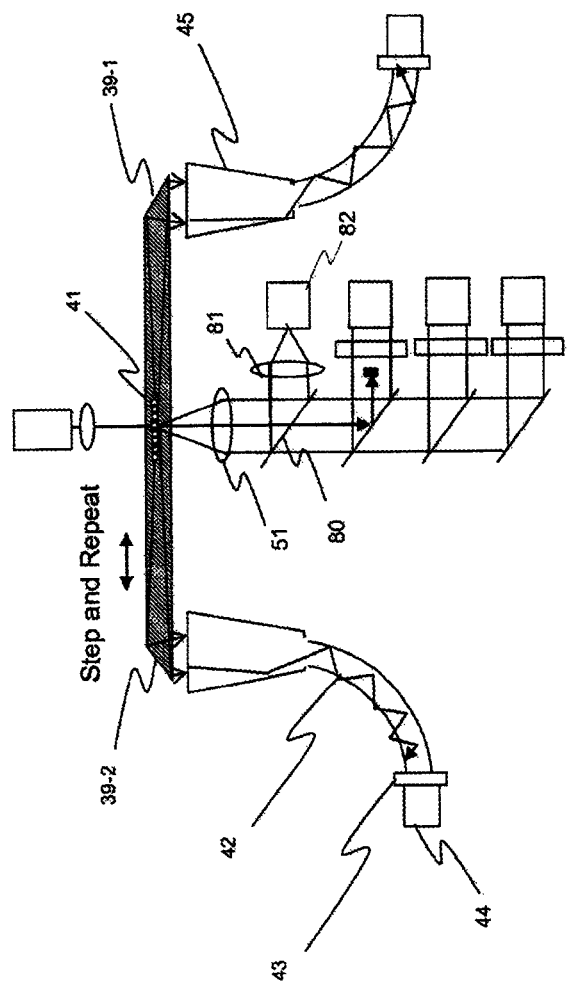
FIG. 7 is a view showing the detection system for sideward scattered light using the disposable chip-type flow cell for multiple samples according to the present invention.

2) Method for Separating Cells and Apparatus for Separating Cells which can Solve A Problem Regarding the Detection of Sideward Scattered Light Using A Disposable Chip for Multiple Samples Next, an embodiment of flow cytometer using a disposable chip-type flow cell with multiple flow paths will be described with reference to FIG. 6 and FIG. 7. In order to measure the multiple samples while satisfying the requirements that cross contamination and carry-over of samples do not occur, eight, sample flow paths are formed on a chip, and eight sample liquid reservoirs 31 are connected thereto respectively, as shown in FIG. 6. Eight chambers 37 in the reservoir 30 are sheath liquid reservoirs. The sheath liquid reservoirs are divided so that the sheath liquids are not mixed in the reservoir 30. Each sample reservoir is disposed in each of chambers. Two ports for connecting sheath liquid flow paths to the sheath liquid reservoirs exist in the each camber. The flows of the sheath liquid and the sample liquid connected to each chamber are controlled by applying air pressure to the each chamber in sequence. That is, waste of the sample liquids and the sheath liquids is avoided by applying air pressure only to the chamber having the sample liquid that is being tested. The size of the cross-section of the flow path is same as the cross-section of the flow path disclosed in FIG. 4. At the time of measurement, the pressure applied upstream is 10 kpa to 20 kpa, and at times other than during measurement, the pressure applied upstream is the same atmospheric pressure that is applied at the downstream end of the flow path. In the chamber, common air pressure is applied to the sheath liquid and the sample liquid so as to feed them downstream. A sheath liquid port 32 is connected to the flow path in the substrate, and the sheath liquid flow paths join to the sample liquid flow path from the left and right sides thereof so that the sheath liquid flows downstream. FIG. 7 shows a cross-sectional view of the chip and an optical system for measurement. The optical detection system using a lens 51 is the same as one described in FIG. 5, except that an optical system capable of monitoring an image of the flow path is added thereto. The optical system includes a reflective mirror with a reflection of 1%, imaging lens 81 and a camera 82. The optical illumination system including the laser and the optical detection system are fixed in place, and the eight flow paths are measured by moving an automatic stage on which the chip is placed. In the chip with eight flow paths, the moving distance corresponding to the width of eight flow paths is 5 mm, because of a limit to the intervals of eight flow paths produced by injection molding. As to the movement of the stage, the laser illumination point is positioned at the No. 1 flow path of the end using the image recognition. Next, a constant pressure is applied to the reservoir connected to the No. 1 flow path, so that the sample liquid is fed only to the No. 1 flow path and then the sample is measured. When the measurement of the sample in the No. 1 flow path is finished, the application of pressure to the upstream reservoir connected to the No. 1 flow path is stopped, and thus the pressure to the reservoir becomes atmospheric pressure. Then, the laser illumination point is positioned at a No. 2 flow path by moving the stage, and the sample is measured by the application of pressure to the reservoir connected to the No. 2 flow path. This procedure is repeated sequentially up to the No. 8 flow path. The measured sideward scattered light is downward reflected at an angle of about 45 degrees at the end face of the flat substrate. Then the light enters the light guiding blocks 45 which is made of transparent resin and positioned on the lower side of the end face. The light goes through an optical fiber connected to the light guiding blocks, and then using the band pass filter 43, the light with same wavelength as the laser illumination light is detected by the photodetectors 44. The sideward scattered signals which are collected and detected by the light guiding blocks on both sides, are added. FIG. 7 shows a method wherein the scattered lights on both sides are detected by the two detectors and converted to signals, and then total signals are added. On the other hand, the sideward scattered light may be measured by connecting the optical fibers connected to the light guiding blocks on either side, to one detector. The width of the light guiding blocks 45 is 10 mm because it is required that the width of the light guiding blocks is broader than the moving distance of the stage corresponding to the width of eight flow paths. Accordingly, using the disposable chip-type flow cell with eight flow paths, a device wherein the forward scattered light, the sideward scattered light, and multiple fluorescence signals of 8 samples can be sequentially detect and measured by one chip, is achieved.

As shown in FIG. 6, multiple flow paths are formed on a transparent flat substrate, and the flow paths are connected to a reservoir 30 at the upstream and a reservoir 34 at the downstream. In order not to mix the sample liquids between the flow paths, the reservoirs are divided with respect to each flow path. FIG. 7 shows the cross-sectional view of the chip and the optical system for measurement. The optical detection system using the lens 51 is the same as one described in FIG. 5, except that the optical system capable of monitoring an image of the flow path is added thereto. The optical system includes a reflective mirror with a reflection of 1%, imaging lens 81 and a camera 82. Using the optical system, the positional relationship of the flow path and the laser illumination point can be recognized by imaging recognition. Thus the position of laser and the position of the flow path are automatically regulated by feeding back the detected positional relationship to the automatic stage moving. The optical illumination system including the laser and the optical detection system are fixed, and the chip is scanned on the automatic stage according to the step-and-repeat manner. As a result, a center region of each of the flow paths may be sequentially illuminated. The sideward scattered light, is downward reflected at an angle of about 45 degrees at the end face of the flat substrate. Then the light enters the light guiding blocks 45 which is made of transparent resin and positioned on the lower side of the end face. The light goes through an optical fiber connected to the light guiding blocks, and then using the band pass filter 43, light with same wavelength as the laser illumination light is transmitted and detected by the photodetectors 44.

Figure 8A:
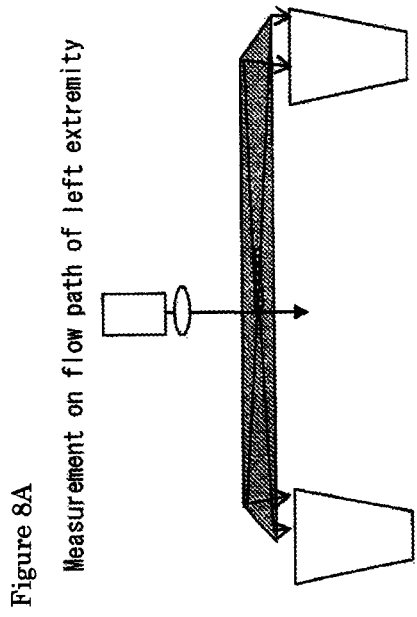
FIGS. 8A and 8B are views showing the relationship between the detection system for sideward scattered light using the disposable chip-type flow cell for multiple samples, and a movement of the chip
Figure 8B:
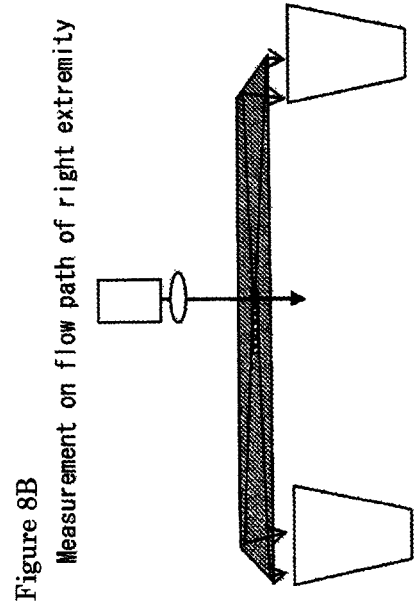

FIG. 8A shows the positional relationship of the chip and the light guiding blocks at both ends when a center of the left-most flow path of the multiple flow paths is illuminated by the laser light. FIG. 8B shows the positional relationship of the chip and the light guiding blocks at both ends when a center of the right-most flow path of the multiple flow paths is illuminated by the laser light. In both cases, the width of the light guiding blocks in the direction of scanning is broader than the extent of the scanning distance, in order that the sideward scattered light reflected on the both ends of the chip enters the light guiding blocks. Further, the sideward scattered signals which are collected in the light guiding blocks and detected are summed, and thus differences of detection sensitivity depending on the flow path used are reduced. As a method for adding the sideward scattered signals, there may be mentioned a method wherein optical fibers connected to the light guiding blocks of both ends are connected to one detector.

Figure 9A:
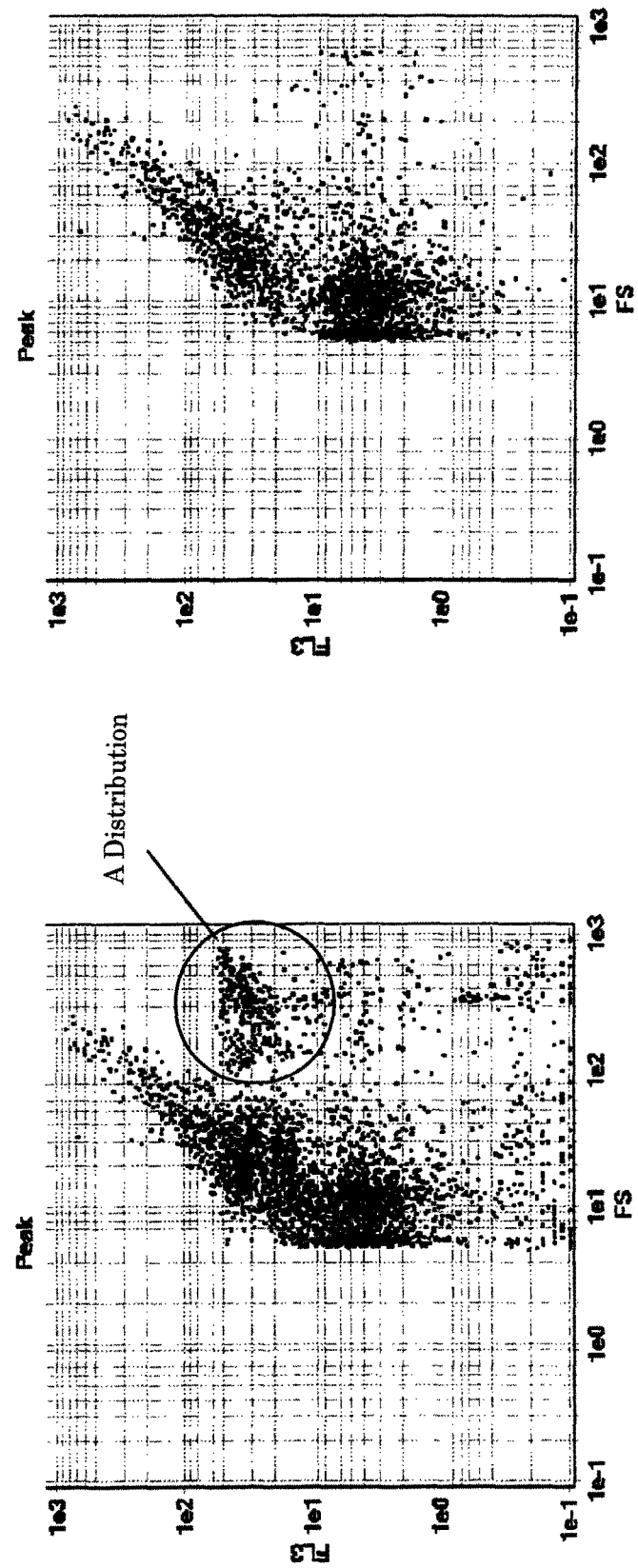
FIGS. 9A and 9B are plots showing that the influence of air bubbles generated when the measurement of all the sample is finished, can be avoided in the flow cytometer using the disposable chip-type flow cell for multiple samples of the present invention.
Figure 9B:
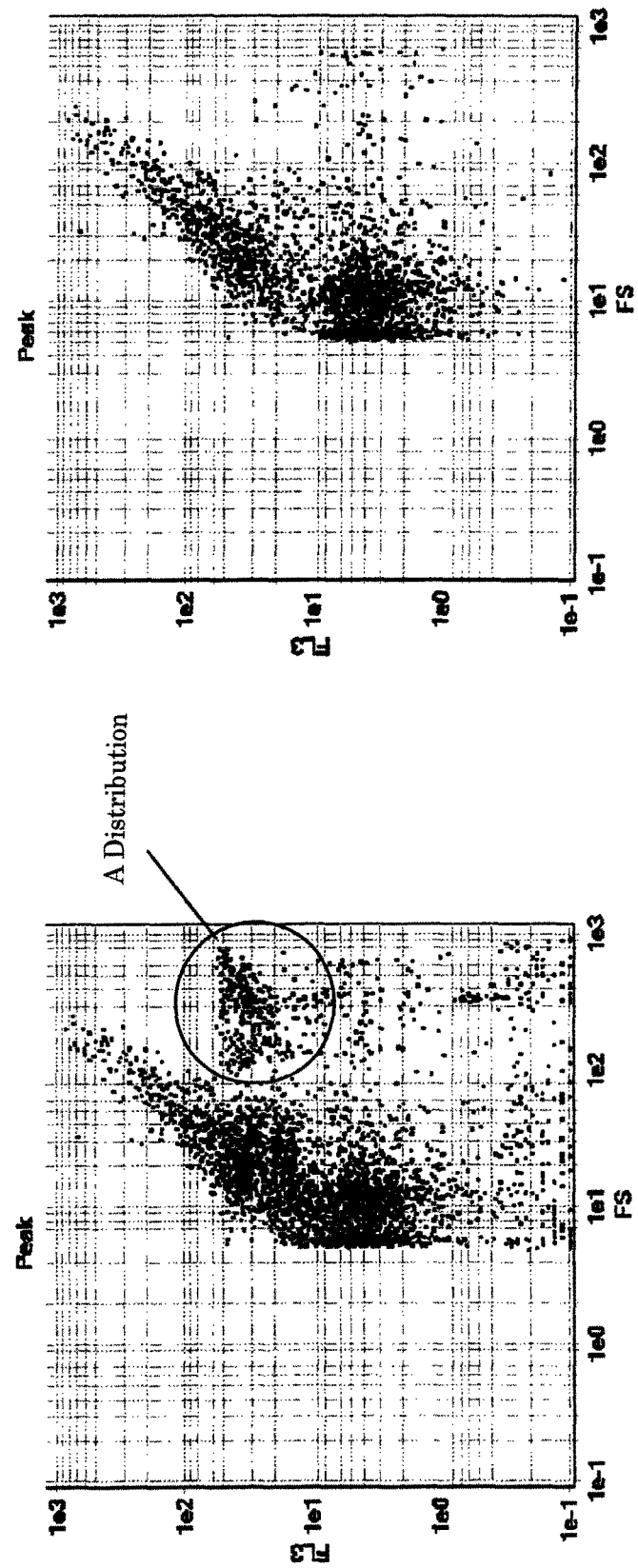

3) Method for Separating Cells and Apparatus for Separating Cells as A Method for Accurately Measuring Particle Concentration Contained in the Sample Liquid To be Tested Next, an example of a method for accurately measuring particle concentration in a liquid will be described by referring FIGS. 6, 9A, and 9B. In order to accurately measure the particle concentration, the entire sample of liquid poured in the sample reservoir may be measured and the resulting cells number divided by the total volume of the sample liquid. In the present invention, the total volume of the sample liquid is measured until the effect of bubbles after a completion of the sample liquid is contained in the resulting data. Then, the data relating to the bubbles is removed from the resulting data after the measurement so that an accurate cell concentration can be obtained. The volume of the sample reservoir 31 described in FIG. 6 is 100 µL. The sample liquid containing cells is poured into the sample reservoir 31, and then a measurement time of 6 minutes and a flow rate of 10 µL/min are set up. In this case, the sample liquid is finished after about 5 minutes, and for the remaining 1 minute, the bubbles are measured. FIG. 9A shows the results of measurement of MCF-7 cells derived from breast cancer, which contains the data relating to bubbles due to the measurement of the entire sample liquid. After the sample liquid is finished, air from the sample reservoir becomes bubbles in the flow path. Then, the bubbles go through a measurement region, and thus the particle numbers in the data are increased. After the sample liquid is finished, a distribution A labeled in FIG. 9A is generated. Forward scattered signals (FS) of the particles in the distribution A are intensive, and thus the particles are larger than cells.

After the measurement, if the data after the detection of bubbles is removed from the data, the distribution A may be deleted while maintaining the distribution of cells and any particles other than cells. This is because the distribution A is derived from the bubbles generated after the sample liquid is finished in the late measurement. Therefore, the any distribution removed together with distribution A may be judged as a distribution derived from bubbles.

In the disposable chip, the flow path is connected to the bottom of the sample liquid reservoir. In a case where 100 µL of the sample liquid is poured to the sample reservoir, and then the entire sample liquid is measured, and the obtained numbers of particles is 10,000, the concentration of the particles should be calculated to 100,000 particles/mL. However, the above result cannot be obtained by the conventional method. This is because bubbles having a distribution different from the particles are frequently generated shortly after the completion of the sample liquid, and the distribution of the bubbles disrupts the counting of the particles. In the conventional flow cytometer, since the sample liquid in a sample container is aspirated from above the sample liquid, it is impossible to measure the entire sample liquid. In the present invention, an accurate concentration of particles in the sample liquid can be measured. The method for measuring the entire sample liquid, which is not subjected to the influence of the bubbles and can accurately measure them, will be described below. The bubbles generate shortly after the completion of uptake of the sample liquid. Therefore, the data consisting solely of the data of particles wherein the distribution data of bubbles are deleted can be obtained, by deleting a set of data shortly before the last detection point, from the measured data. The entire sample liquid was measured using the chip disclosed in Patent literature 14 (the inventor thereof is the same as the present inventor). The resulting data including the distribution of the bubbles is shown in FIG. 9A. An abscissa axis is forward scattered light and a longitudinal axis is fluorescence signal intensity. FIG. 9B shows a data wherein the later part of data is deleted from the whole measured data. That is, it is found that the distribution of particles having high intensity of forward scattered light is deleted. One of the distributions derived from the bubbles is focused on, and then a set of data from the last detection point is deleted until the focused distribution disappears. As a consequence, the data of distribution of bubbles can be deleted. Accordingly, it is possible to measure the entire sample liquid, and obtain an accurate particle concentration.

Figure 10A:
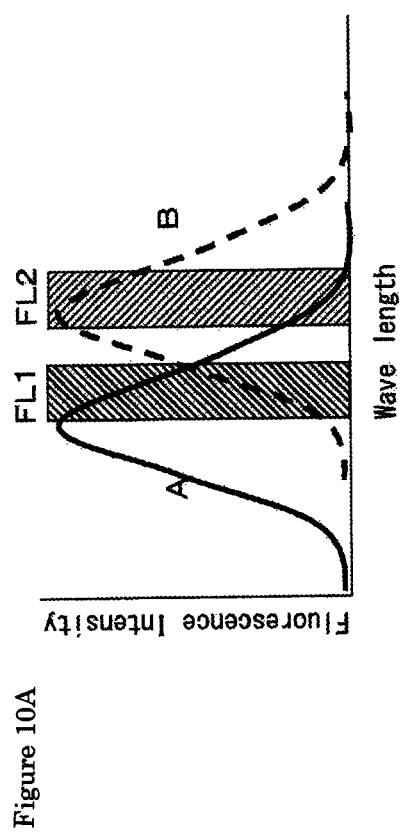
FIG. 10A is a graph showing fluorescence spectra and the two regions of fluorescence detection wavelength (FL1 and FL2).

4) Multidimensional Data Analysis Method by Flow Cytometer, Indication Method thereof, and Apparatus thereof FIG. 10(A) shows two different fluorescence wavelength detection bands, i.e. FL1 and FL2, and spectra of two kinds of fluorescence molecules. i.e. A and B. A method in which the cells are stained by the two kinds of fluorescence A and B, and an abundance ratio in a cell is measured using the fluorescence signals in bands FL1 and FL2 will be described. The relationship between the fluorescence detection signals in FL1 and FL2, for a given fluorescence is determined by the shape of the fluorescence spectrum. That is, the ratio between the measured values in FL1 and FL2 is constant. For example, when the area of fluorescence A in the detection wavelength region FL1 is referred to as $A1$, and the area of fluorescence A in the detection wavelength region FL2 is referred to as $A2$, the fluorescence signal intensity ratio of FL1 to FL2 is $A1/A2$. This is indicated by the following formula:

$$FL1/FL2 = A1/A2 \tag{1}$$

The above formula may be converted to the following formula for a logarithmic chart.

$$\text{Log } FL1 = \text{Log } FL2 + \text{Log}(A1/A2) \tag{2}$$

Similarly, in the case of the fluorescence B, the fluorescence signal intensity ratio of FL1 to FL2 is $B1/B2$. This is indicated by the following formula:

$$FL1/FL2 = B1/B2 \tag{3}$$

The above formula may be converted to the following formula for a logarithmic chart.

$$\text{Log } FL1 = \text{Log } FL2 + \text{Log } B1/B2 \tag{4}$$

Figure 10B:
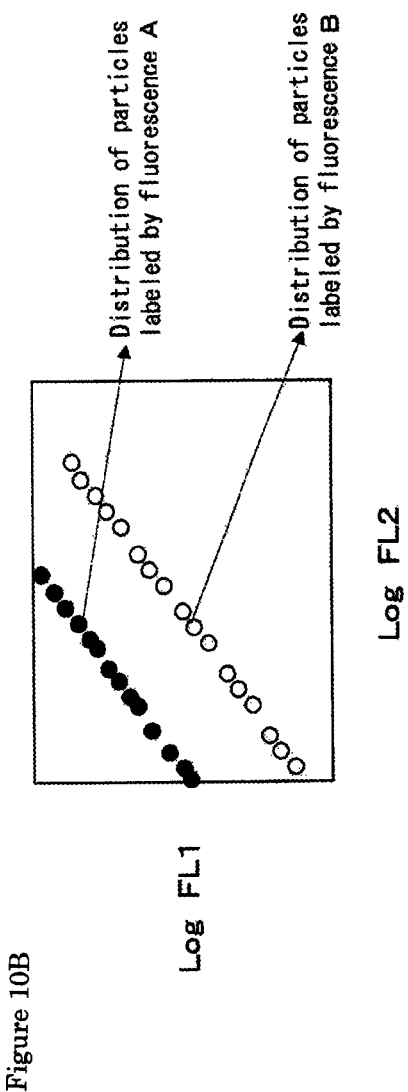
FIG. 10B is a schematic view showing the distributions of particles labeled by two fluorescent reagent molecules in a scatter plot of FL1 and FL2.

Therefore, when the cells stained by the fluorescence molecule A are measured, the cells are distributed on the line shown by black circles in the double logarithmic scatter plot between FL1 and FL2 shown in the FIG. 10(B). Similarly, when the cells stained by the fluorescence molecule B are measured, the cells are distributed on the line shown by white circles. As shown in the scatter plot, particles with different fluorescence spectra are distributed respectively on two straight lines with different intercepts on the longitudinal axis. Next, particles including fluorescence molecule A and fluorescence molecule B will be discussed. When the amounts of fluorescence molecule A and of fluorescence molecule B are referred to x and y respectively, signal intensity FL1 and FL2 are indicated by the following formulas (5) and (6) respectively.

$$FL1 = A1x + B1y \tag{5}$$

$$FL2 = A2x + B2y \tag{6}$$

From the formulas (5) and (6), next formula is calculated.

$$\text{Log } FL1 = \text{Log } FL2 + \text{Log } [(A1x+B1y)/(A2x+B2y)] \tag{7}$$

Figure 11A:
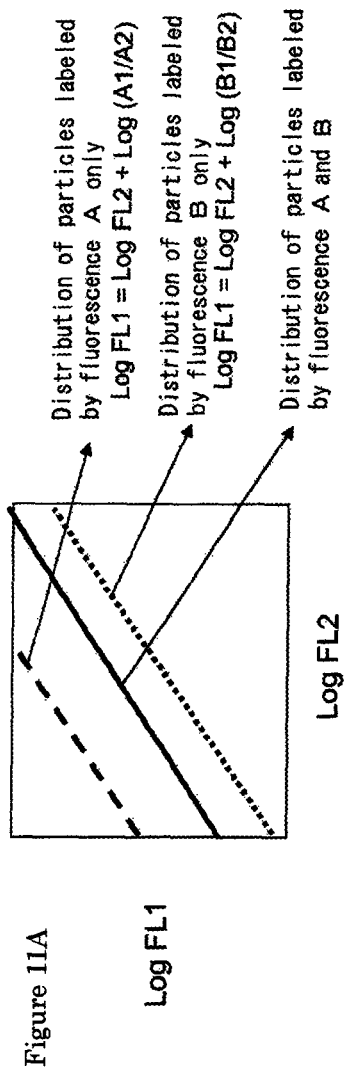
FIGS. 11A and 11B are views showing an analysis method for double stained cells according to the present invention. The graph shown in FIG. 11A can be converted to the graph shown in FIG. 11B when the data of the graph in FIG. 1A is shown using log FL1/FL2 as a longitudinal axis.

This formula (7) defines a straight line positioned between the straight line indicated by the formula (2) and the straight line indicated by the formula (4), as shown in FIG. 11(A). The straight line indicated by formula (7) is shifted according to the ratio between x and y.

The following formula in which x/y is calculated from FL1/FL2 may be obtained from the ratio between formula (5) and formula (6).

$$x/y = [(B1/B2)-(FL1/FL2)]/[(FL1/FL2)-(A1/A2)](B2/A2) \tag{8}$$

Figure 11B:
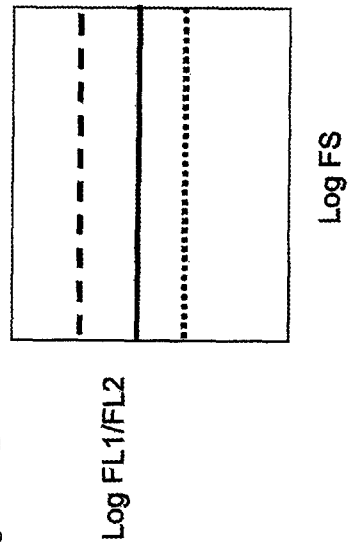

In formula (8), $B1/B2$ indicates a constant value obtained from a sample stained only by fluorescence B. $A1/A2$ indicates a constant value obtained from sample stained only by fluorescence A. Further, $FL1/FL2$ indicates measured data of the sample. $B2/A2$ indicates a constant value obtained from a the ratio between FL2 values of a sample stained by fluorescence molecule A and a sample stained by fluorescence molecule B, where the molecular numbers of A and B is same in the respective samples. Therefore, x/y value can be obtained with respect to each detected cell. As shown in FIG. 11B, when the logarithm of FL1/FL2 is shown on the longitudinal axis, the value on the longitudinal axis is dependent on the value of x/y. Information on x/y and a information on cell size can be presented together by adopting the forward scattered signal intensity (FS) as the abscissa axis, as shown in FIG. 11(B). Further, a signal other than FS can be selected as the abscissa axis. In the present invention, an important value for analysis, such as FL1/FL2 shows on the axis of the graph as an index for analysis. In consequence, it is possible that the multidimensional information is presented as one dimensional information as a whole. Further, a quantitative judgment can be achieved by determining a threshold level on the index.

Figure 12:
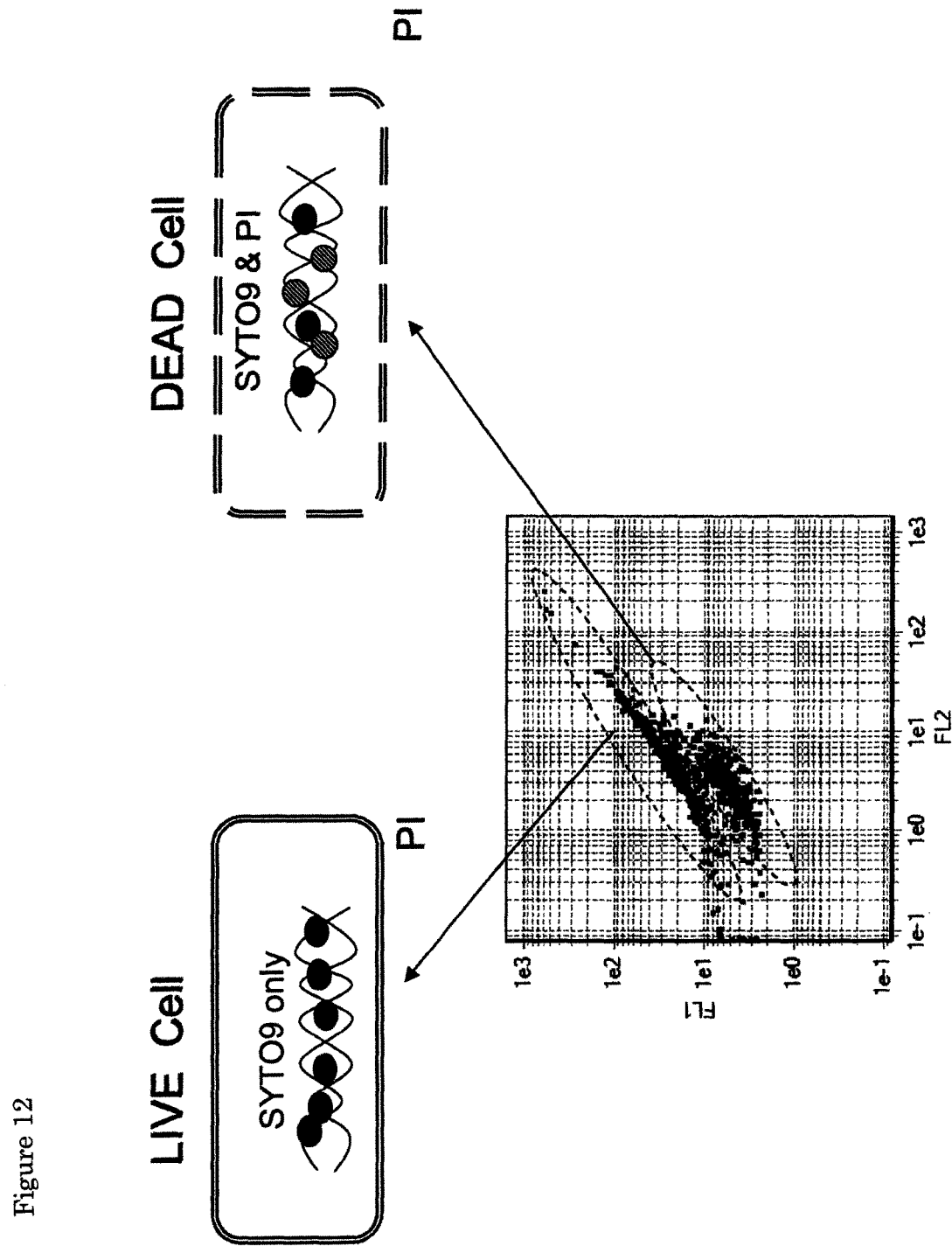
FIG. 12 is a view for explaining a conventional analysis method for determining whether cells are alive or dead.

Next, an example of above data analysis will be described. A conventional analysis method for determining cell viability using two nuclear dyes i.e. nuclear dye SYT09 capable of penetrating the biological membrane and a nuclear dye PI not capable of the penetrating biological membrane is shown in FIG. 12. On the other hand, in the present invention, an index for determining cell viability is defined, and then cell viability is automatically determined on the basis of a predetermined threshold level of the index. This method will be described by referring FIGS. 12 and 13. The wavelength of FL1 is about 500 nm to 550 nm, and the wavelength of FL2 is 570 nm to 610 nm. As shown in FIG. 12, in the conventional analysis for determining cell viability, a distribution of the live cell (i.e. distribution of cells only stained by SYTO9) and a distribution of the dead cells (i.e. distribution of cells stained by both of SYTO9 and PI) should be discriminated. The means of the discrimination is dependent on image recognition by an operator. On the other hand, in the present invention, a quantitative index for automatically determining cell viability is defined, and then live cell and dead cell are discriminated by a predetermined threshold level for determination of the index. Specifically, in order to analyze cell viability, cells are stained using two nuclear dyes i.e. nuclear dye SYT09 capable of penetrating cell membrane and a nuclear dye PI not capable of penetrating cell membrane according to the following protocol. 1.5 µL of 3.34 mM SYTO 9 and 1.5 µL of 30 mM PI are added to 1 mL of PBS to prepare a dye solution. 2 µL of the dye solution is added to the sample liquid, and a staining reaction is carried out for 20 minutes in the dark.

FIG. 12 shows the results obtained by staining MCF-7 cells according to the above procedure and measuring fluorescence. In the scatter plot, the distribution of the live cells which are stained only by SYTO9 is shown as a linear distribution. On the other hand, in the distribution of the dead cells, membranes of the cells are destroyed and thus the cells are further stained by PI. Therefore, the cells are doubly stained. In the distribution of the dead cells, the amount of SYTO9 and the amount of PI are kept at an almost constant rate. Therefore, the position of the distribution of the dead cells is shown as a linear distribution shifted on the downside compared to the position of the distribution of the live cells.

Next, FL1/FL2 is defined according to formula (9):

$$FL1/FL2=\Delta \quad (9)$$

Then, when the formula (9) is converted to formula (10):

$$\text{Log } FL1=\text{Log } FL2+\text{Log } \Delta, \quad (10)$$

Figure 13:
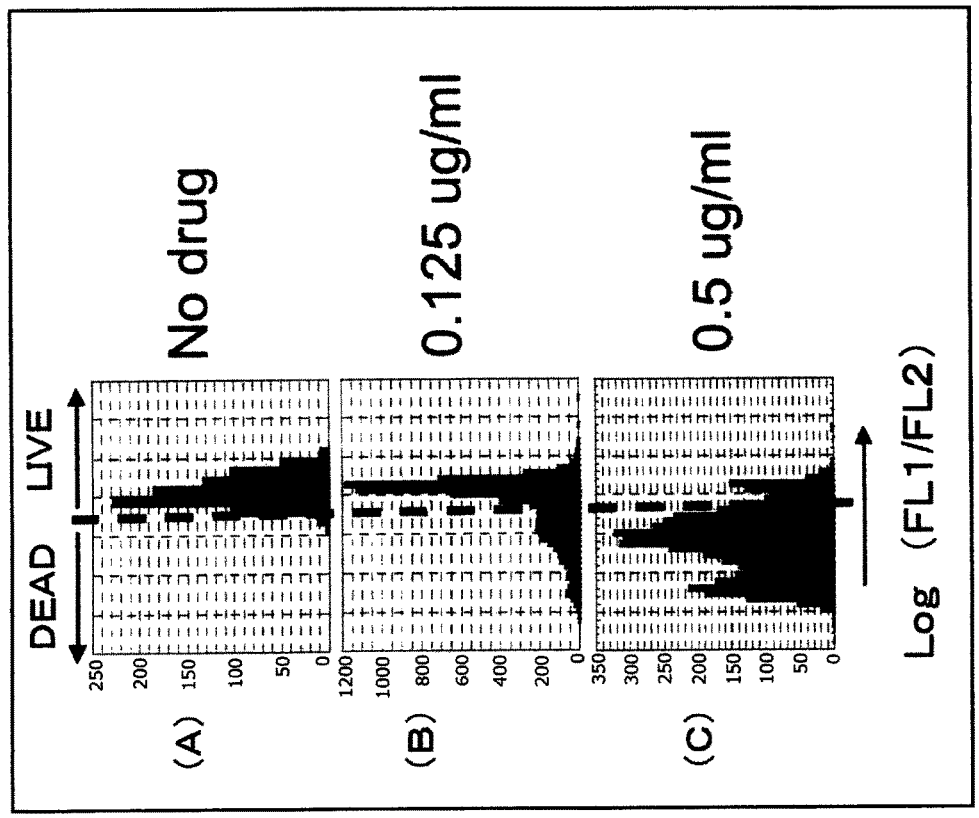
FIG. 13 shows graphs (A, B, and C) demonstrating results obtained by applying an analysis method using multicolor staining of the present invention to an analysis for determining whether bacteria are alive or dead.

The logarithm of FL1/FL2 is seen to be the intercept of the formula (9) on the longitudinal axis. When the logarithm of FL1/FL2 of the distribution of the live cells is compared to one of the dead cells, the logarithm of FL1/FL2 on the distribution of live cells is higher than for the dead cells. FIG. 13 is the graphs showing the effect of antibacterial agent to *Pseudomonas aeruginosa*. The antibacterial agent was added to the bacteria, and allowed to keep for a predetermined time. Then the bacteria were stained by SYTO9 and PI for 20 minutes, and the measured FL1/FL2 is shown as a distribution histogram. When the antibacterial agent is not added thereto, a distribution having single peak is shown. On other hand, when the antibacterial agent is added thereto, a distribution containing cells having lower value of FL1/FL2 appears. Further the results wherein the distribution containing cells having lower value of FL1/FL2 increases with the increasing concentration of the antibacterial agent. The threshold level for determining life or death is shown as a dashed line in FIG. 13. The threshold level is defined as a boundary line between a distribution of 100% live bacteria of and a distribution of 100% dead bacteria, which are obtained by preliminary measuring them respectively. Whether particles (such as cells or bacteria) are dead or alive can be automatically determined by using the threshold level as a standard. Therefore, it is found that FL1/FL2 is useful as an index for automatically determining life or death. The above matter will be described below by referring to the formulae. FL1/FL2 is defined by formula (9). Then, when the formula (9) is converted to formula (10) it is found that the logarithm of FL1/FL2 means the intercept of a linear line on the distribution of dead cells or dead cells. It is expected that the value of FL1/FL2 become low by changing from live cell to dead cell. Therefore, FL1/FL2 is useful as the index for analyzing life or death.

Figure 14:
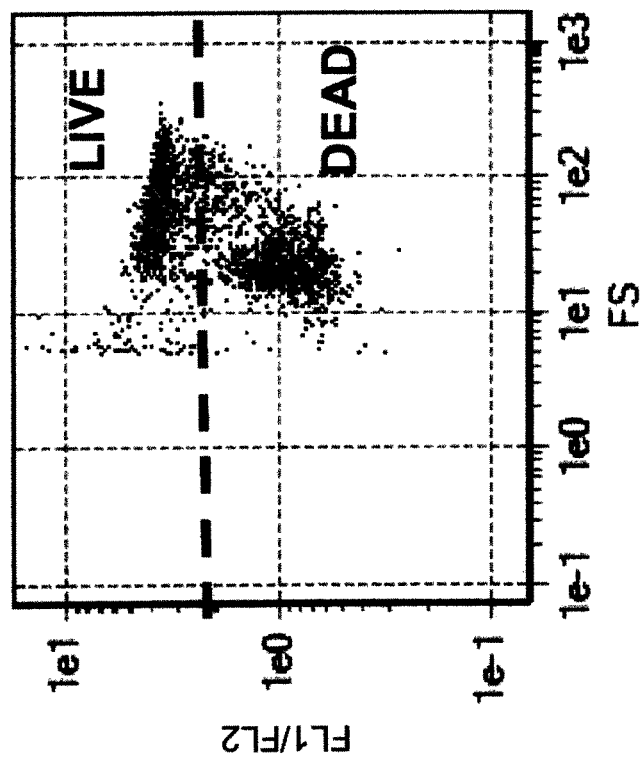
FIG. 14 is an example of multidimensional information showing a determination of life or death of cells using an index of the present invention.

FIG. 12 shows the scatter plot used as the conventional analysis for determining cell viability. On the other hand, FIG. 14 shows a scatter plot in which the same results disclosed in FIG. 12 are illustrated using the index for determining life or death of the present invention. The information of cell viability and information of cell size can be presented in one dimensional scatter plot by adopting FL1/FL2 as a longitudinal axis and the forward scattered light intensity signals (FS) which shows cell size as an abscissa axis. From the scatter plot of FIG. 14, it is found that, for the MCF-7 cells that are measured, the size of the dead cells is smaller than that of the live cells.

Figure 15:
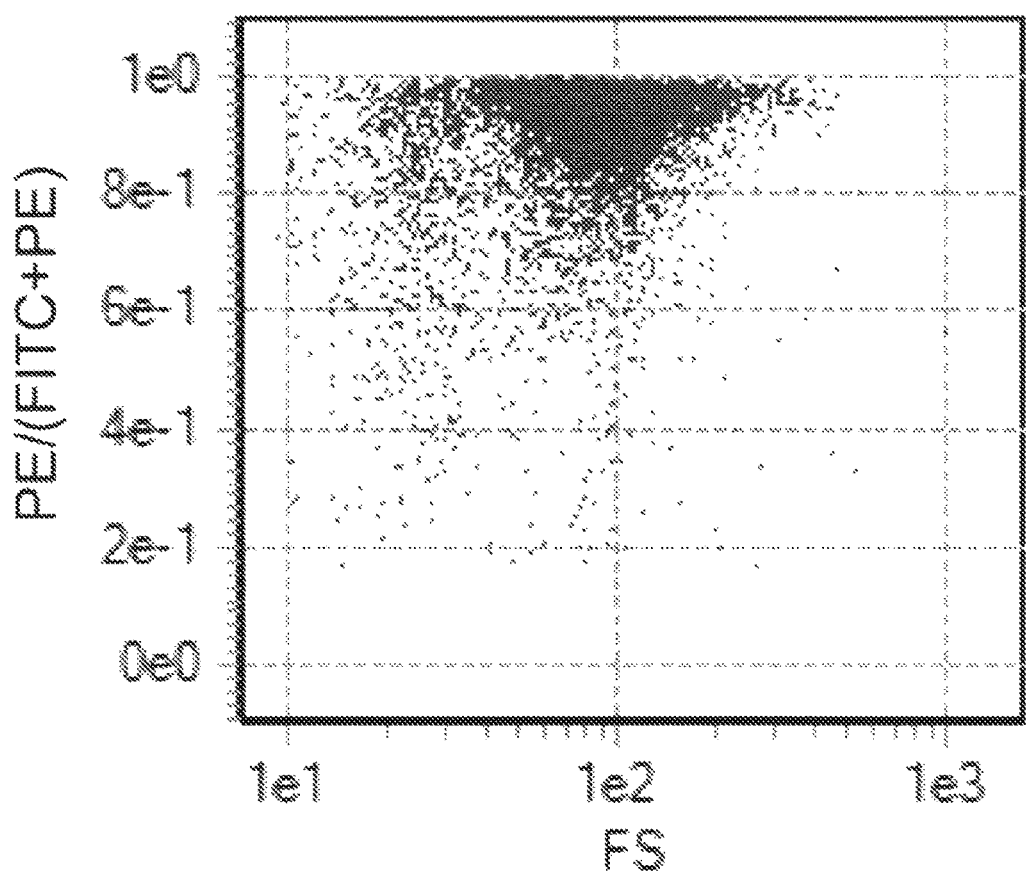
FIG. 15 is another example of multidimensional information showing a determination of life or death of cells using an index of the present invention.

As mentioned above, as a method for expressing the multidimensional data in flow cytometer, an index defined by a formula using some signal intensities may be adopt as an axis of the graph, for the aim of measurement. As a consequence, the amount of information contained in the two dimensional scatter plot can be increased. FIG. 15 is an indicated example wherein the two kinds of cell surface markers are stained using the FITC labeled antibody and the PE labeled antibody, and resulting data are shown by adopting PE/(FITC+PE) as the longitudinal axis and FS as the abscissa axis. In the above index PE/(FITC+PE), PE or FITC is the amount of fluorescence after a correction, and the amount is proportional to the number of fluorescence molecules. The above index is defined as an index showing a proportion of expression between the two kinds of surface markers. Thus, FIG. 15 is the indicated example showing in one graph that the proportion of expression of two kinds of surface markers is dependent on the size of cells. Regarding the proportion of expression of each cell, the value thereof can be analyzed by the use of the value of the index. Further, as an index for determining whether the detected particle is a single cell or several aggregated cells, the index "(signal pulse area)/(signal pulse duration)" or the like may be defined. For example, floating cells such as leucocytes are circulated as a single cell. However, it is not always true that cancer cells etc. are circulated in the blood as a single cell. In the above analysis, it is necessary to analyze the number of cells regardless of whether or not cells are aggregated. Therefore, the above index is useful for analyzing whether or not cells are aggregated.

Accordingly, it is advantageous to define an appropriate index for analysis by the use of a formula using several signals, and to quantitatively analyze a property of each cell by the value of the index. The merits of the above are as follows. The information of three or more signals can be shown in a one dimensional scatter plot, by showing multidimensional information as a single index. Further, the quantitative judgment as to each cell can be achieved by preliminary determining a threshold level on the index. Thus, this method is useful for quantitative medical diagnosis.

INDUSTRIAL APPLICABILITY

The present invention is useful as (1) a cell sorter, (2) a flow cytometer capable of detecting sideward scattered light, (3) an apparatus for accurately measuring cell concentration, (4) an apparatus for multicolor staining analysis without a fluorescence correction, and a method for cell separation and analysis; which satisfy requirements that a carry-over and a cross contamination of samples do not occur.

REFERENCE SIGNS LIST

1 . . . Sample liquid flow path
2 . . . Sheath liquid flow path
3 . . . Illumination light
4-1 . . . Sorting flow path (PULL side)
4-2 . . . Sorting flow path (PUSH side)
5 . . . Sorting reservoir
6 . . . Filter
7-1, 7-2 . . . electromagnetic valve
8-1 . . . Negative constant-pressure pump
8-2 . . . positive constant-pressure pump
9-1 . . . Cell to be separated (Cell of interest)
9-2 . . . Cell not to be separated
10 . . . Sample liquid reservoir
11 . . . Sample liquid collection reservoir
20 . . . Sheath liquid reservoir 22 . . . Sheath liquid port
23 . . . Sheath liquid collection port
24 . . . Sheath liquid collection port
25 . . . substrate for chip
27 . . . Flow path
31 . . . Sample liquid reservoir
32 . . . Sheath liquid port
34 . . . Discharged liquid reservoir
35 . . . Sample liquid collection reservoir
36 . . . Sample liquid
37 . . . Sheath liquid reservoir
39-1, 39-2 . . . Reflecting plane for detecting sideward scattered light
40 . . . Laser beam scan region
41 . . . Flow path
50 . . . Laser light source
51 . . . objective lens
52 . . . Laser light
53 . . . Region between the sorting flow paths 4-1 and 4-2
54, 55, 56 . . . Dichroic mirror
57, 58, 59 . . . Band pass filter
60 . . . Spatial filter (shielding plate) for blocking transmission laser light
61 . . . Photo diode
62, 63 . . . Photomultiplier tube
64 . . . AD converter
69 . . . AD converter
70 . . . Keyboard
71 . . . Display

The invention claimed is:

1. A method for sorting a cell particle in a solution by using a cell sorting apparatus,
wherein the cell sorting apparatus comprises a sample solution reservoir formed on a substrate, a main flow path formed in the substrate for flowing sample solution from the sample solution reservoir, a first branched flow path and a second branched flow path both connected to the main flow path from both sides of the main flow path at a branched flow path region thereof such that the first branched flow path and the second branched flow path form a straight sorting flow path perpendicularly crossing the main flow path over the branched flow path region thereof, and a downstream flow path connected to a downstream of the branched flow path region of the main flow path for receiving the sample solution which was not collected into the second flow path, wherein the second branched flow path comprises a sorting reservoir and a pump, wherein a first end of the sorting reservoir is connected to the main flow path and a second end of the sorting reservoir is connected to the pump, the method comprising:
storing a sample solution in the sample solution reservoir and applying a constant gas pressure to the sample solution so that the sample solution stored in the sample solution reservoir flows through the sample solution flow path at a predetermined velocity;
illuminating the sample solution flowing in an illumination region of the main flow path upstream of the branched flow path region, and identifying a cell particle of interest contained in the sample solution by detecting a scattered light or fluorescence generated from the cell particle and outputting a detection signal;
upon receiving the detection signal, determining a delayed timing that the identified cell particle of interest reaches the branched flow path region after the cell particle of interest passed the illumination region; and
applying a pushing pressure from the first branched flow path and a pulling pressure from the second branched flow path to the sample solution flowing in the main flow path simultaneously at the delayed timing so that a flow rate in the straight sorting flow path is faster than a flow rate in the main flow path and the sample solution containing the cell of interest is separated from the main flow path and introduced into the sorting reservoir of the second branched flow path.

2. The method of claim 1, wherein the first branched flow path is connected to a first constant pressure pump maintaining a pressure higher than that of the main flow path via a first electromagnetic valve, and the pump of the second branched flow path is a second constant pressure pump maintaining a pressure lower than that of the main flow path via a second electromagnetic valve, and the first electromagnetic valve and the second electronic valve are simultaneously opened at the delayed timing so that the pushing pressure and pulling pressure are applied from the first and second branched flow path to cause the flow of the straight sorting flow path.

3. The method of claim 1, wherein the delayed timing is set based on the time period that the identified particle of interest takes to reach the branched flow path region after passing the illumination region.

4. The method of claim 1, wherein magnitudes of the pushing pressure and the pulling pressure are adapted to be nearly the same so that the flow caused by the pushing pressure and pulling pressure is substantially limited to be within a width of the straight sorting flow path.

5. The method of claim 1, wherein the first branched flow path and the second branched flow path are both filled with a sorting fluid, and a volume of sorting fluid pushed from the first branched flow path by the pushing pressure is adapted to be substantially equal to the volume of fluid pulled from the second branched flow path by the pulling pressure.

6. The method of claim 1, wherein velocity of the flow of fluid in the straight sorting flow path caused by the pushing pressure and pulling pressure is faster than the velocity of the flow of sample solution in the main flow path.

* * * * *